(12) United States Patent
Terman et al.

(10) Patent No.: US 10,314,903 B2
(45) Date of Patent: Jun. 11, 2019

(54) COMPOSITIONS AND METHODS FOR TREATMENT OF CANCER

(71) Applicants: David S Terman, Pebble Beach, CA (US); David Bradley, Grand Forks, ND (US)

(72) Inventors: David S Terman, Pebble Beach, CA (US); David Bradley, Grand Forks, ND (US)

( * ) Notice: Subject to any disclaimer, the term of this patent is extended or adjusted under 35 U.S.C. 154(b) by 0 days.

(21) Appl. No.: 15/611,717

(22) Filed: Jun. 1, 2017

(65) Prior Publication Data
US 2018/0028639 A1 Feb. 1, 2018

Related U.S. Application Data

(60) Provisional application No. 62/483,769, filed on Apr. 10, 2017, provisional application No. 62/344,863, filed on Jun. 2, 2016.

(51) Int. Cl.
*A61K 39/00* (2006.01)
*A61K 39/085* (2006.01)

(52) U.S. Cl.
CPC ...... *A61K 39/085* (2013.01); *A61K 2039/515* (2013.01); *A61K 2039/54* (2013.01); *A61K 2039/55555* (2013.01); *A61K 2039/585* (2013.01); *A61K 2039/6006* (2013.01)

(58) Field of Classification Search
None
See application file for complete search history.

(56) References Cited

PUBLICATIONS

Bhardwaj et al., Small Amounts of Superantigen, When Presented on Dendritic Cells, Are Sufficient to Initiate T Cell Responses, J. Exp. Med. 9 The Rockefeller University Press, vol. 178 Aug. 1993 633-642.
Havari et al., Expression of the B7.1 Costimulatory Molecule on Pancreatic B Cells Abrogates the Requirement for CD4 T Cells in the Development of Type 1 Diabetes, J Immunol 2004.

*Primary Examiner* — Patricia Duffy

(57) ABSTRACT

Here we show that SEG/SEI presented from a HLA-DQ8 (HLA-DQB*0302 and HLA-DQA*0301) platform prevent the de novo outgrowth (vaccination) of Lewis lung carcinoma (LLC) and B16-F10 melanoma and retard the growth of established tumors with no significant toxicity. Vaccination of DQ8 tg mice with irradiated LLC or B16-F10 melanoma followed by SEG/SEI immunization and live tumor challenge resulted in 100 and 66% survival respectively for 200 days compared to a median survival of 20 days for untreated controls (p<0.001). In vaccination studies, DQ8 tg mice showed a surge in IFNγ serum levels reaching 3000 fold above baseline devoid of a parallel spike in TNFα levels above baseline levels. Presentation of the SEG/SEI superantigen from a MHC-DQ8 platform, therefore, augments the therapeutic index of these SAgs inducing a tumoricidal response against Lewis lung carcinoma and B16 melanoma accompanied by a sharp increase of therapeutic IFNγ levels absent toxic levels of TNFα.

Figure 1:
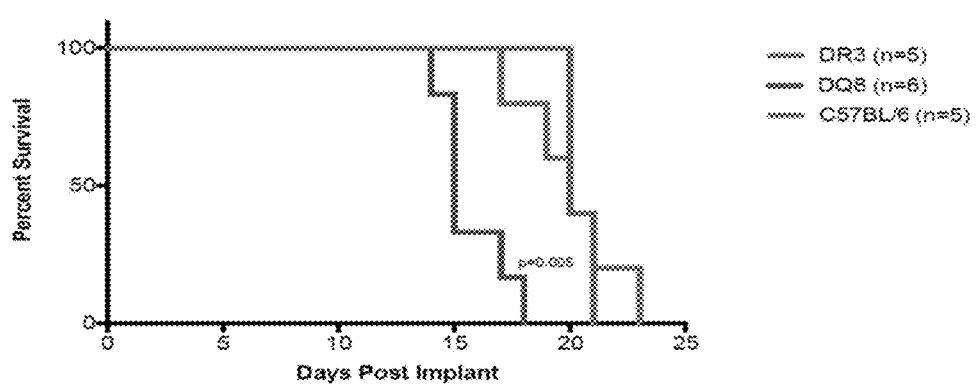

2 Claims, 13 Drawing Sheets
Specification includes a Sequence Listing.

Lewis Lung Carcinoma

COMPOSITIONS AND METHODS FOR TREATMENT OF CANCER

CROSS REFERENCE TO RELATED DOCUMENTS

The provisional patent application 62/483,769 filed on Apr. 10, 2017 and provisional patent application 62/344,863, filed on Jun. 2, 2016 are incorporated in entirety by reference with their reference in the instant regular application. All references cited herein along with their references are incorporated in entirety by reference.

BACKGROUND OF THE INVENTION

Field of the Invention

The invention is in the fields of genetics, immunology, medicine and covers compositions and methods for treatment of cancer

Discussion of the State of the Art

*Staphylococcus aureus* produces a broad range of exoproteins, including staphylococcal enterotoxins (SEs) and staphylococcal-like enterotoxins. To date, 23 different SEs are recognized designated SE A to X. All these toxins share superantigenic properties by stimulating a large proportion of T cells after binding to the major histocompatibility complex (MHC) class II molecule and crosslinking specific vβ regions of the T-cell receptor (TCR). This interaction results in polyclonal T-cell activation and secretion of cytokines such as interleukin-2 (IL-2), interferon gamma (IFNγ), tumor necrosis factor alpha (TNFα), and nitric oxide (NO). Several members of this group are implicated in the pathogenesis of toxic shock syndrome and food poisoning and exhibit anti-tumor activity in animal models. Unprocessed SAgs bind directly to MHCII molecules outside the polymorphic antigen-binding groove used by conventional peptides and are capable of activating T lymphocytes at picomolar concentrations. Superantigens bind to selective Vβ chains of the T cell receptor (TCR) and activate up to 20% of resting T cells relative to conventional antigens which stimulate less than 1% or the T cell repertoire (Marrack and Kappler Science 248: 1066-72 (1990)); Terman et al., Clin. Chest Med. 27: 321-34 (2006)).

When used to treat cancer in humans SAgs have been unsuccessful due to the presence of pre-existent neutralizing antibodies that inactivate and remove them from the circulation. In a clinical trial with SEA, every patient exhibited elevated baseline levels of neutralizing antibodies against SEA (Alpaugh et al., Clin. Cancer Res. 4: 1403 (1993). Attempts to remove the epitopes in SEA reactive with the neutralizing antibodies did not improve the effectiveness of this agent in patients with significant levels of neutralizing antibodies (Hawkins et al., Clin. Cancer Res. 22:3172-81 (2016)). Further attempts at dosing to achieve SEA levels greater than the those of neutralizing antibodies failed to improve the tumor killing and led to greater toxicity (Cheng J D et al., J. Clin. Oncol. 22:602-9 (2004)).

In humans, unmodified SAgs SEA or SEB have been associated with severe dose-limiting cardiopulmonary toxicity that has nullified their ability to exert a therapeutic effect. While SEA and SEB were used together in mice to induce a tumoricidal effect in mice, each of these agents induced stage 3-4 toxicity in humans or toxic shock in humanized MHCII transgenic mice (Llewelyn M et al., J. Immunol. 172:1719-1726 (2004)); Kominsky et al., Int. J. Cancer: 94: 834-841 (2001); Alpaugh et al., Clin. Cancer Res. 4: 1403-1411 (1993); Young et al., Am. J. Med. 75: 278-286 (1983); Taneja V and David C S, Immunol. Rev. 169: 67-79 (1999)). With full knowledge of the toxic effect of SEA or SEB as used alone in humans, the skilled person would be dissuaded from using both together to treat human cancer. Attempts to modify this toxicity by eliminating MHCII binding sequences in the SEA molecule led to modestly improved toxicity but conferred no added antitumor efficacy (Hawkins, R E et al., Clin. Cancer Res. 22:3172-81 (2016).

While superantigen induced tumor killing is mediated largely by IFNγ, the generation of cytotoxic T cells, toxicity is ascribed to SAg induction of TNFα which leads to the appearance of the full or partial picture of toxic shock (Miethke J. Exp. Med. 175: 91-98. (1992)). Most superantigens simultaneously activate large quantities of TNFα along with INFγ with ratios of INFγ:TNFα ranging from 2:1 to 5:1 (Norrby-Teglund et al., Eur. J. Immunol. 32: 2570-2577 (2002); Llewelyn et al., J. Immunol. 172:1719-1726 (2004); Tilahun er al., Mediators of Inflammation doi.org/10.1155/2014/468285; Rajagopalan et al., Tissue Antigens 71:135-145 (2007)). Toxic effects of TNFα induced in humanized MHCII tg mice by most SAgs surface early after SAg treatment placing a severe limitation on the ability of SAgs to display tumoricidal effects. The acute lethal toxicity exhibited by superantigens SEB and SPEA in humanized MHC-DQ tg mice due to induction of high levels of TNFα is a powerful disincentive to the use of these or related SAgs to treat cancer. Since SEI induces the highest levels of TNFα among all SEs (Terman et al., Frontiers in Cellular and Infection Microbiology 3: 1 doi: 10.3389/fcimb.2013.00038) its use alone to treat cancer would be counterintuitive. Likewise, SEG's weak ability to induce IFNγ in human T cells would dissuade the skilled scientist from using it to treat cancer (Terman et al., supra 2013)). Hence, based on individual cytokine profiles of SEG and SEI generated by human T cells (Terman et al., supra 2013) it could not be assumed that that SEG and SEI would induce a surge in IFNγ levels in vivo while barely raising TNFα levels as demonstrated herein during in vivo studies in MHC-DQ8 tg mice. In these mice SEG and SEI combined to induce INFγ:TNFα ratios exceeding 800:1 during successful anti-tumor treatment devoid of acute or chronic toxicity. The prior art could also not predict that SEG and SEI used together in doses 10-15 fold higher than highly toxic SEB and SPEA in humanized MHCII-DQ8 transgenic mice could induce tumor killing with minimal toxicity. Such a selective induction by dual superantigens SEG and SEI in humanized DQ8 tg mice of tumor killing IFNγ absent a parallel surge in toxicity-inducing TNFα in vivo is unprecedented. (Welcher et al., J. Infect. Dis. 186:501-10 (2002); Llewelyn Metal., J. Immunol. 172:1719-1726 (2004)); Terman et al., Frontiers in Cellular and Infection Microbiology 3: 1 doi: 10.3389/fcimb.2013.00038); Tilahun A Y Mediators of Inflammation doi.org/10.1155/2014/468285; Rajagopalan G et al., Tissue Antigens 71:135-145 (2007)).

Objects and Advantages

Accordingly, several objects and advantages of this invention are as follows:

The claimed invention remedies the above concerns by producing a vastly improved cancer therapy with no significant toxicity. For this task, we selected superantigens SEG and SEI which have been shown to be devoid of neutralizing antibodies in human sera (Holtfreter et al., Infect. Immun. 72: 4061-71 (2004)). This has been attributed to weak transcription and translation from their resident operon inside *Staphylococcus aureus* (Xu and McCormick Front. Cell. Infect. Microbiol. 2: 1-11 (2012)). Hence, the claimed method overcomes the problem of neutralizing antibodies The claimed invention using SEG and SEI overcomes the toxicity of previously used SAgs while retaining potent tumoricidal effects. This was discovered while using humanized transgenic MHC-DQ8 mice to test the anti-tumor effects of SEG and SEI. Surprisingly, DQ8 mice treated with these two SAgs survived a lethal challenge of Lewis lung carcinoma or B16F10 melanoma for more than 200 days and showed no significant toxicity. Unexpectedly, we further discovered that, despite SEI's ability to induce the highest levels of TNFα in human T cells of all SAgs (Terman et al., supra 2013), in MHC-DQ tg mice SEI used together with SEG induced very low levels of TNFα while simultaneously producing massive quantities of IFNγ. IFNγ has the ability to exert direct anti-tumor effects on tumor cells or indirect tumoricidal activity via activation of immune cells (Ikeda H Cytokine and Growth Factor Rev. 13 95-109 (2002); Tan J et al., J. Immunother. 21:48-55. (1998); Parker BS Nature Rev. Cancer 16: 131-140 (2016)). Ratios of serum levels of IFNγ:TNFα observed during combined SEG and SEI treatment ranged from 3000:1 to 800:1 far exceeding those noted in the course of SEB and SPEA immunization in humanized transgenic mice (Bavari S et al., J. Infect. Dis. 186:501-10 (2002); Norrby-Teglund A et al., Eur. J. Immunol. 32: 2570-2577 (2002); Llewelyn M et al., J. Immunol. 172: 1719-1726 (2004); Tilahun A Y et al., Mediators of Inflammation doi.org/10.1155/2014/468285; Rajagopalan G et al., Tissue Antigens 71:135-145 (2007)). These elevated IFNγ levels promoted the tumor killing effect of SEG and SEI while low TNFα levels precluded toxicity. Surprisingly, in humanized DQ tg mice, SEG and SEI combined to produce a highly favorable therapeutic index i.e., potent tumoricidal effect in mice devoid of toxicity accompanied by therapeutic levels of INFγ and non-toxic levels of TNFα.

Further objects and advantages of this invention will become apparent from a consideration of the drawings and ensuing description.

SUMMARY OF INVENTION

*Staphylococcus aureus* SEG and SEI superantigens derived from the enterotoxin growth cluster (egc) are notably devoid of human seroreactive neutralizing antibodies that have hampered the use of the classic superantigens as cancer therapeutics. Here we show SEG/SEI presented from a HLA-DQ8 (HLA-DQB*0302 and HLA-DQA*0301) platform prevent the de novo outgrowth (vaccination) of Lewis lung carcinoma (LLC) and B16-F10 melanoma and retard the growth of established tumors with no significant toxicity. Vaccination of DQ8 tg mice with irradiated LLC or B16-F10 melanoma followed by SEG/SEI immunization and live tumor challenge resulted in 100% and 66% survival respectively or 200 days compared to a median survival of 20 days respectively for untreated controls ($p<0.001$). In vaccination studies, DQ8 tg mice showed a surge in IFNγ serum levels reaching 3000 fold above baseline devoid of a parallel spike in TNFα levels. Splenocytes from vaccinated DQ8 tg mice displayed 3 fold greater CD4+-mediated B16-F10 melanoma cytotoxicity. The anti-tumor response devoid of toxicity appears to be mediated by a selective spike in INFγ and CD4+ cytotoxic memory T cells unattended by a parallel surge of TNFα. Presentation of the SEG/SEI superantigen from a MHC-DQ8 platform, therefore, augments the therapeutic index of these SAgs inducing a tumoricidal response against Lewis lung carcinoma and B16 melanoma accompanied by a sharp increase of therapeutic IFNγ levels absent toxic levels of TNFα.

BRIEF DESCRIPTION OF DRAWINGS

FIG. 1. Survival of C57BL/6, DQ8 tg and DR3 tg mice following challenge with live LLC cells is comparable indicating no significant allogeneic effect in the rejection of LLC by DR3 and DQ8 mice. DR3 and DQ8 mice showed significantly shorter survival than C57BL/6 mice indicating no significant allogeneic contribution to the tumor killing. Indeed, all three strains bear the H-2b phenotype.

FIG. 2. Anti-tumor effect in DQ8 tg mice of vaccination with irradiated LLC melanoma on day −13 followed by SEG/SEI immunization on days −6 and −3 with live tumor implant on day 0. 66% of these mice survived to 200 days post live tumor implant.

FIG. 3. Anti-tumor effect of LLC tumor implanted in DQ8 mice followed by treatment with SEG/SEI showing prolonged survival relative to the untreated control ($p<0.001$).

FIG. 4. Attenuation of B16F10 melanoma outgrowth in DQ8 tg mice by vaccination with irradiated B16F10 melanoma cells followed by immunization with SEG, SEI individually or together on days 6 and 9. Results show that combined SEG/SEI immunization prolonged survival significantly.

FIG. 5. Both DQ8 tg and B16F10 mice were implanted with B16F10 melanoma on day 0 and treated with SEG and SEI on days 6 and 9. Survival of established DQ8 mice after B16F10 melanoma implant and treatment with SEG and SEI exceeds that of the similarly treated C57BL/6 mice ($p=0.01$)

FIG. 6 A,B. Cytokine levels obtained after vaccination with irradiated LLC or B16F10 melanoma on day 0 followed by immunization on days 6 and 10 with SEG/SEI. Cytokine levels obtained on days 7 showed 3000 fold surge in IFNγ levels days unassociated with a comparable surge of other toxicity inducing cytokines TNFα and IL-2.

FIG. 7. Cytotoxicity of splenocytes from DQ tg mice on day 0 after vaccination with irradiated B16F10 melanoma on day −13 and immunization with SEG/SEI on days −6 and −3. Data shows a striking increase in CD4+-mediated cytotoxicity of B16F10 melanoma cells at 50:1 ratio. This CD4+ mediated effect correlates with the surge in serum levels of IFNγ at this time in the immunization schedule and points to a CD4+, TH-1 cytokine response consisting of IFNγ predominantly as the major mediator of the anti-tumor effect of the vaccine in the DQ tg mice.

FIG. 8. T cell proliferation of naïve C57Bl/6 splenocytes in response to SEA, SEB, SEG and SEI is shown along with for each superantigen. Notably, DQ tg splenocytes are more mitogenic in response to SEG and SEI relative to C57BL/6 mice.

FIG. 9 A,B,C. Schematic of the lentiviral vectors with EF1 promoters with DQ8A1 and/or DQ8B1 gene insertions is shown.

FIG. 10 A,B. Flow cytometry of 4T1 cells transduced with DQ8A1 and DQ8B1 genes using the lentiviral vectors in Figure-9 indicating surface expression of DQ8A1 and DQ8B1 on the 4T1 tumor cells FIG. 11. Schematic of the human β-globin lentiviral vector wherein the $\beta^{AS3}$ anti-sickling gene coding region is replaced by DQ8A1 and DQ8B1 genes. Also shown are LCR and downstream genes. HS2 (1203 bp), HS3 (1213 bp), and HS4 (954 bp) sequences, the 3' globin enhancer, the 266-bp β-globin promoter ((βp) and the $β^S$-globin coding region. The HIV-1 LTR is displayed with a 3' SIN deletion; ψ indicates packaging signal; SD and SA, splice donor and acceptor sites, respectively; RRE, Rev-responsive element; cPPT/CTS, central polypurine tract or DNA flap/central termination sequence; and WPRE, woodchuck hepatitis virus post-transcriptional regulatory element.

DESCRIPTION OF THE PREFERRED EMBODIMENTS

*Staphylococcus aureus* produces a broad range of exoproteins, including staphylococcal enterotoxins and staphylococcal-like enterotoxins. All these toxins exhibit superantigenic properties activating a large proportion of T cells after binding to the major histocompatibility complex (MHC) class II molecule and crosslinking specific vβ regions of the T-cell receptor (TCR). This interaction results in polyclonal T-cell activation and secretion of cytokines such as interferon gamma (IFNγ), tumor necrosis factor alpha (TNFα), and nitric oxide (NO). Several members of this group have a major role in the pathogenesis of toxic shock syndrome and food poisoning and exhibit anti-tumor activity in animal models. Unprocessed SAgs bind directly to MHCII molecules outside the polymorphic antigen-binding groove used by conventional peptides and are capable of activating T lymphocytes at picomolar concentrations. Superantigen binding to selective vβ chains of the T cell receptor (TCR) activates up to 20% of resting T cells relative to conventional antigens which stimulate less than 1% of the T cell repertoire. (Marrack, P., and Kappler J Science 248: 1066-72 (1990)). Terman, D. S. et al., Clin. Chest Med. 27: 321-34 (2006)).

MHC class II molecules in mice and humans are the primary docking sites for bacterial superantigens. In humans, there are three major isotypes of HLA class II, designated HLA-DP, HLA-DQ and HLA-DR. HLA-DR and HLA-DQ exist in multiple allelic forms. HLA-DQ class II molecule is a heterodimer consisting of an alpha (DQA) and a beta chain (DQB), both anchored in the membrane. It plays a central role in the immune system by presenting peptides derived from extracellular proteins. Class II molecules are expressed predominantly on antigen presenting cells such as B Lymphocytes, dendritic cells, macrophages. The alpha chain is approximately 33-35 kDa. It is encoded by 5 exons; exon 1 encodes the leader peptide, exons 2 and 3 encode the two extracellular domains, and exon 4 encodes the transmembrane domain and the cytoplasmic tail. Within the DQ molecule both the alpha chain and the beta chain contain the polymorphisms specifying superantigen and peptide binding specificities.

By determining the affinity, conformation and sequence of T-cell epitopes presented by different HLA class II alleles, HLA class H polymorphism controls the strength and quality of the immune response to superantigens. Such polymorphism also governs the strength of SAg-induced T cell proliferation and qualitative/quantitative differences in cytokine profiles (Bell J I et al., Immunol. Rev. 84: 51-71. (1985); Turner D. Vox. Sang. 87 Suppl 1 87-90 (2004); Ovsyannikova I G et al., J. Infect. Dis. 193: 655-63. (2006); Monos D S et al., Human Immunol. 66: 554-62 (2005)). In a typical example, superantigen streptococcal pyrogenic exotoxin A induced higher proliferative responses and production of IFNγ, TNFα and IL-2 when presented by MHCII DQA1*010/DB1*03 as compared to MHCDR1, DR4 and DR5 (Norrby-Teglund et al., Eur. J. Immunol. 32: 2570-2577 (2002)). Despite these different outcomes from MHCII binding preferences among SAgs, a cytokine profile has yet to emerge that displays a massive IFNγ surge with minimal TNFα that could be used for anti-tumor treatment in humans without significant toxicity as shown in the claimed method.

Animal models have contributed significantly to the knowledge of the mechanisms involved in SAg induced tumor killing. The advent of the HLA class II transgenic (HLA-DQ8-tg) mice provided an opportunity to study SAg in an animal model with a sensitivity to SAgs similar to that of humans (Welcher et al., supra (2002); Taneja V and David C S. Immunol. Rev. 169: 67-79 (1999)).

The egcSEs comprise five genetically linked staphylococcal enterotoxins, SEG, SEI, SEM, SEN and SEO and two pseudotoxins which constitute an operon present in up to 80% of *S. aureus* isolates. The egcSEs are structurally homologous and phylogenetically related to classic SEA-E (Jarraud, S. et al., J. Immunol. 166: 669-77 (2001); Becker, K. et al., J. Clin. Microbiol. 41:1434-9 (2003))). Despite their broad distribution, human serum levels of neutralizing antibodies directed against the egcSEs are significantly lower than those directed to the classic SEs (Holtfreter et al., Infect. Immun. 72: 4061-71 (2004)). This has been ascribed to defective mRNA translation and impaired extracellular secretion (Xu and McCormick Front. Cell. Infect. Microbiol. 2: 1-11 (2012)). Interestingly, septicemia associated with the egcSEs appears to be less severe clinically than that linked to the classic SEs (Ferry et al., Clin. Microbiol. Infect. 14: 546-554 (2008)). In recent studies, the egc SEs showed a hierarchy of T cell activation and the ability to generate nitrites and TH-1/TH-2 cytokines (Terman et al., Front Cell Infect Micro 3: 1 doi: 10.3389/fcimb.2013.00038).

Of the egcSEs, SEG consists of 233-residues corresponding to a mature protein of 27 kDa, which shares 41 to 46% amino acid sequence identity with other members of the SEB family (10). SEG occurs with higher frequency than classical SEs in *S. aureus* isolates (Munson, et al., Infect. Immun. 66: 3337-3348 (1998); Banks et al., J. Infect. Dis. 187: 77-86 (2003); Becker et al., Clin. Microbiol. 41: 1434-1439 (2003).) Notably, SEG shows substitutions in three key residues located in the conserved binding surface for murine Vβ8.2, resulting in an affinity for Vβ8.2 which is 40 to 100-fold higher than that reported for other members of SEB subfamily and the highest reported for any wild type SAg-TCR couple. SEG also retains the fast dissociation rate characteristic of SAgs that allows sequential binding to several other TCR vβ molecules (Fernandez M M, J. Biol. Chem. 286: 1189-1195 (2011).) Despite its high affinity for MHCII SEG generates lower levels of TH-1 cytokines, IFNγ, TNF-α, IL-2 than the other egcSEs and classical SEA.

SEI is encoded in the egc operon of *S. aureus* and associated with toxic shock syndrome, food poisoning and various veterinary diseases. Comparison of the SEI crystal structure with those of SEH and SPEC bound to MHC class II reveals a zinc-dependency that targets key residues of the peptide associated with the MHCII β-chain (Fernandez M M J. Biol Chem 281: 25356-25364 (2006)). SEI activation of human T cells produced the highest levels of IFNγ, TNFα and IL-2 of all egcSEs and SEA (Terman et al., supra 2013)). Surprisingly, when SEG and SEI are used together in DQ8 tg mice, the prevailing cytokine phenotype is a massive increase in IFNγ serum levels devoid of a spike in TNFα level above baseline. This suggests that SEG downregulates SEI's ability to activate TNFα in vivo while permitting full expression of SEI's ability to activate therapeutic levels of INFγ.

During human cancer trials using SEA and SEB, significant dose limiting toxicity was observed. This is largely due to their ability to induce polyclonal activation of T cells resulting in the production of high levels of TH-1 cytokines namely IFNγ and TNFα. IFNγ is known to induce anti-tumor effects while TNFα produce the acute sequalae of toxic shock (Miethke et al., supra (1998); Fraser PLoS Biol. 2011 September; 9(9):e1001145. doi: 10.1371/journal.pbio.1001145; Parker et al., supra (2016)). With both SEA and SEB, cardiopulmonary toxicity dominated the clinical picture before therapeutic benefits could be realized (Alpaugh et al., supra 1998; Young et al., supra 1983). Other SAgs have been recognized as poor candidates for cancer treatment because they produce insufficient IFNγ, or sufficient IFNγ but also toxic levels of TNFα.

The inventors have uncovered a remedy for problem. By using SEG and SEI together in humanized DQ8 mice we have found that these agents show striking ant-tumor effects against melanoma and Lewis lung carcinoma. Importantly, the cytokine profile induced by these agents in the course of vaccination with irradiated tumor cells and SEG/SEI displays a profound spike in IFNγ nearly 3000 fold above baseline attended by minimal changes from baseline in toxicity-inducing TNFα and IL-2. As articulated below, these mice also showed robust anti-tumor effects against both de novo or established tumors with minimal toxicity. In contrast, superantigens SEB and SPEA induced toxic shock and death within 7 hours after administration of a 10 fold lower dose respectively than either SEG or SEI in similar humanized MHCII mice. The lethal shock was associated with a surge in TNFα to toxic levels of 600 to 1000 pg/ml (Llewelyn M et al., J Immunol. 172:1719-26 (2004); Welcher et al., J. Infect. Dis. 186:501-10 (2002). Other SAgs were considered to be poor candidates for cancer treatment because they induced either insufficient IFNγ, or they produced sufficient IFNγ along with high levels TNFα and IL-2. Until the instant invention, SAgs used alone or as a plurality that produced high levels of IFNγ with low levels of TNFα had not been identified.

In the present invention, we deploy transgenic mice expressing human HLA DQ8 instead of mouse MHCII to present superantigens to murine T cells. Here, we show for the first time that combined SEG and SEI administration to HLA-DQ mice bearing B16F10 melanoma or Lewis lung carcinoma induces a significant survival advantage. Notably, DQ8 tg mice vaccinated with irradiated tumor cells followed by SEG/SEI immunization showed 100% survival of B16 melanoma and Lewis lung carcinoma up to 200 days following live tumor implant. Statistically significant prolonged survival was also induced by SEG/SEI delivered after live tumor challenge with B16 melanoma or Lewis lung carcinoma in DQ8 tg mice. The mice showed no toxicity of the SEG/SEI treatment including weight loss, cachexia or death.

Surprisingly, the TH-1 cytokine profile induced by SEG and SEI in DQ tg mice during vaccination with irradiated tumor cells and SEG/SEI displayed a profound spike in IFNγ levels to nearly 3000 fold above baseline attended by minimal increases in toxicity-inducing TNFα and IL-2 level. In this setting, these mice showed robust anti-tumor effects against both de novo or established tumors with minimal toxicity. The ratios of INFγ:TNFα ranged from 3000:1 to 800:1 after SEG/SEI immunization. In contrast, superantigens SEB and SPEA induced toxic shock and death within 7 hours after administration of 10 fold lower doses respectively than either SEG or SEI to similar humanized MHCII. Toxic doses of SPEA and SEB were associated with parallel surges of IFNγ and TNFα and INFγ:TNFα ratios of 0.6 and 3:1 respectively (Llewelyn M et al., J Immunol. 172:1719-26 (2004); Bavari S et al., J. Infect. Dis. 186:501-10 (2002). Hence, unexpectedly SEG and SEI induced an optimal ratio of IFNγ:TNFα in DQ8 tg mice that led to long term survival after lethal tumor challenge.

The SEG-SEI-DQ8 combination of claimed invention is unique in that it provides a robust anti-tumor effect with minimal toxicity in humanized MHC-DQ8 mice wherein other SAgs have produced severe toxicity at 10 fold lower doses. Combining SEG and SEI in DQ8 tg mice resulted in highly surprising and unexpected protection of mice from a lethal challenge with lung cancer and melanoma cells. Both tumors represent classic models of their respective human tumors. We discovered that the profound protection afforded by combined SEG and SEI is due to a highly unique 3000 fold surge of IFNγ levels in the serum. Because of the lethality of related superantigen SPEA in DQ8 tg mice the skilled scientist would not be motivated to deploy SEG and SEI in 10 to 12 fold higher doses to treat cancer in these mice. Knowing full well that SEI was the most potent producer of both IFNγ and TNFα of all SAgs tested would have deterred the skilled person from using this agent. Surprisingly and unexpectedly SEI used together with SEG in DQ8 mice skewed the cytokine profile toward IFNγ excess with minimum TNFα and IL-2 levels leading to remarkable effectiveness of these agents against de novo or established tumors. The SEG-SEI-induced cytokine profile and attendant dramatic anti-tumor effect against lung cancer and melanoma in DQ tg mice is unprecedented and could not be predicted from the prior art.

Methods

Mice

Female, 6-8 week-old C57BL/6 and HLA-DQ8αβ (DQA*0301/DQB*0302), referend herein as HLA-DQ8, mice were used for experiments. The HLA-DQ mice were originally a gift from Dr. Chella David (Mayo Clinic, Rochester, Minn., USA) and their generation was described previously (35-37). Briefly, DQA*0301/DQB*0302 were introduced into mice devoid of murine H2-A and H2-E expression. HLA-DQ8 genotypes were confirmed via PCR and protein expression was confirmed using flow cytometry. Mice were maintained in pathogen-free conditions within the Center for Biological Research at the University of North Dakota. (Lamoureux J J et al., Arthritis Research & Therapy, 8(4), R134. http://doi.org/10.1186/ar2023).

Cell Culture

B16-F10 (ATCC□ CRL-6475™) murine melanoma cells and Lewis lung carcinoma were obtained from American Type Culture Collection and maintained in complete Dulbecco's Modified Eagle's Medium (DMEM) (ATCC) containing 10% heat inactivated FBS (Atlanta Biologicals), according to manufacturer recommendations, including 50 IU/ml Penicillin and 50 □g/ml Streptomycin (MP Biologicals). C57BL/6 and HLA-DQ8 splenocytes were harvested, processed into single cell suspensions, and used throughout the experiments and maintained in complete DMEM or RPMI. CD4 and CD8 cells were isolated from C57BL/6 and HLA-DQ8 splenocytes using EasyStep™ CD4 and CD8 negative selection kits (Stemcell Technologies) in accordance with manufacturer specifications. All cells were counted using a hemocytometer, and cell viability was determined via trypan blue exclusion (>95% viability used).

Superantigens

Purified, recombinant SEG and SEI were obtained from Aldeveron (Fargo, N. Dak.) at a final concentration of 1 mg/ml in phosphate buffered saline (PBS), pH 7.4.SEA and SEB were obtained from Toxin Technology (Sarasota, Fla.). All reagents were kept at either 4° C. or −20° C. and subject to only 1 freeze-thaw cycle.

Staphylococcal Enterotoxins SEG, SEH, SEI, SEJ, SEK, SEL, SEM, SEN, SEO, SEP, SEQ, SER, SEU Production of the above staphylococcal enterotoxins are described in full in US patent application PCTUS05/022638 filed Jun. 27, 2005 which is incorporated by reference in entirety. New Staphylococcal enterotoxins G, H, I, J, K, L and M (SEG, SEH, SEI, SEJ, SEK, 30 SEL, SEM, SEN, SEO, SEP, SEQ, SER, SEU; abbreviated below as "SEG-SEU") were described in Jarraud, S. et al., J. Immunol. 166: 669-677 (2001); Jarraud S et al., J. Clin. Microbiol. 37: 2446-2449 (1999) and Munson, S H et al, Infect. Immun. 66:3337-3345 (1998). SEG-SEU show superantigenic activity and are capable of inducing tumoricidal effects. The homology of these SE's to the better-known SE's in the family ranges from 27-64%. Each induces selective expansion of TCR Vβ subsets. Thus, these SEs retain the characteristics of T cell activation and Vβ usage common to all the other SE's. RT-PCR was used to show that SEH stimulates human T cells via the Vα domain of TCR, in particular Vα (TRAV27), while no TCR Vβ-specific expansion was seen. This is in sharp contrast to all other studied bacterial superantigens, which are highly specific for TCR Vβ. Vβ binding superantigens form one group, whereas SEH has different properties that fit well with Vα reactivity. It is suggested that SEH directly interacts with the TCR Vα domain (Petersson K et al, J Immunol. 170:4148-54 (2003)). SEG and SEH of this group and other enterotoxins including SPEA, SPEC, SPEG, SPEH, SME-Z, SME-Z2, (see below) utilize zinc as part of high affinity MHC class H receptor. Amino acid substitution(s) at the high-affinity, zinc-dependent class II binding site are created to reduce their affinity for MHC class II molecules. Jarraud S et al., 2001, supra, discloses methods used to identify and characterize egc SEs SEG-SEM, and for cloning and recombinant expression of these proteins. The egc comprises SEG, SEI, SEM, SEN, SEO and pseudogene products designated γ/ent 1 and γ/ent. Purified recombinant SEN, SEM, SEI, SEO, and SEGL29P (a mutant of SEN) were expressed in *E. coli* Recombinant SEG, SEN, SEM, SEI, and SEO consistently induced selective expansion of distinct subpopulations of T cells expressing particular Vβ genes. Jarraud S et al., 2001, supra, indicates that the seven genes and pseudogenes composing the egc (enterotoxin gene cluster) operon are co-transcribed. The association of related co-transcribed genes suggested that the resulting peptides might have complementary effects on the host's immune response. One hypothesis is that gene recombination created new SE variants differing by their superantigen activity profiles. By contrast, SEGL29P failed to trigger expansion of any of 23 Vβ subsets, and the L29P mutation accounted for the complete loss of superantigen activity (although this mutation did not induce a major conformational change). It is believed that this substitution mutation located at a position crucial for proper superantigen/MHC II interaction.

Overall, TCR repertoire analysis confirms the superantigenic nature of SEG, SEI, SEM, SEN, SEO. These investigators used a number of TCR-specific mAbs (Vβ specificity indicated in brackets) for flow cytometric analysis: E2.2E7.2 (Vβ2), LE89 (Vβ3), IMMU157 (Vβ|35.1), 3D11 (Vβ5.3), CRI304.3 (Vβ6.2), 3G5D15 (Vβ7), 56C5.2 (Vβ8.1/8.2), FIN9 (Vβ9), C21 (Vβ11), S511 (Vβ12), IMMU1222 (Vβ13.1), JIJ74 (Vβ13.6), CAS 1.1.13 (Vβ14), Tamayal.2 (Vβ16), E17.5F3 (Vβ17), pA62.6 (Vβ18), ELL1.4 (Vβ20), IG125 (Vβ21.3), IMMU546 (Vβ22), 5 and HUT78.1 (Vβ23). Flow cytometry also revealed preferential expansion of CD4+ T cells in SEI and SEM cultures. By contrast, the CD4/CD8 ratios in SEO-, SEN-, and SEG-stimulated T cell lines were close to those in fresh PBL.

Recombinant and biochemical preparation of the egc SEs is given in U.S. 60/799,514, PCTUS05/022638, U.S. 60/583,692, U.S. 60/665,654, U.S. 60/626,159 which are incorporated by reference and their references in their entirety. Our most current methodology for manufacture of SEG and yielding up to 300 mg of SEG with 98% purity is given as follows.

The prokaryotic expression cassette for the SEG was codon optimized and built synthetically and the gene was cloned into the pET24b(+) expression plasmid (kanamycin resistant) at the Ndel restriction site to avoid the addition of any tags onto the protein. Following the gene sequence, two STOP codons were inserted to prevent any read-through onto the His tag sequence present on the 3' end of the MCS in the pET24b(+) vector. Signal sequences utilized by *Staphylococcus aureus* for protein activation and posttranslational shuttling were excluded leaving only the amino acid sequence of the mature peptide. The lyophilized DNA was suspended in 10 mM Tris/1 mM EDTA (pH 8) in a Class 100 BSC and then aliquoted at 200 ng/vial (20 ng/μl). The vials were frozen at −80° C.

Growth and Cell Lysis

1. The pET24b-SEG is transformed into BL21 (DE3) Veggie™ and expressed using an auto-induction medium (TBII derivative containing 0.4% lactose). The culture is grown for 20 hours at 30° C., 200 rpm, resulting in ~20 g/L wet weight biomass (harvested by centrifugation).

2. The cells are resuspended in a solution containing 50 mM Tris-HCl, 5 mM EDTA, 10 mM BME, and 1% Triton X-100. The cell suspension is sonicated using a Branson Sonifier at a 50% Duty Cycle and an Output Power of 4 for a total sonication time of 1 min/gram.

3. The lysate is clarified by centrifugation at 15,000×g for 30 minutes. The resulting pellets are resuspended in the same solution and treated to a second round of sonication and clarification.

4. The lysates from each round of sonication are pooled prior to the first 5 chromatography step (approx. 1500 mg of soluble protein is extracted per liter of culture)

Chromatography and Buffer Exchange

1. The clarified lysate is loaded onto a Q/SP Sepharose (mixed bed ion exchange) column and the load flow is collected for subsequent purification.

2. The load flow through from the Q/SP chromatography is diluted with a 50 mM MES, pH 5.5 buffer, 0.45 pM filtered, and loaded onto a SP Sepharose column. A gradient is run from 0-300 mM NaCl in 50 mM MES, pH 5.5 and fractions are collected, neutralized with Tris, and analyzed with SDS-PAGE.

3. Selected fractions from the CEX capture are pooled for further purification. The pooled post-CEX capture solution is diluted with an equal volume of 4.0 M $(NH_4)_2SO_4$, 50 mM Tris, pH 8.0, 0.45 pm filtered, and loaded onto an Octyl Sepharose Fast Flow column. A gradient is run from 2.0-1.0 M $(NH_4)_2SO_4$ and fractions are collected. Samples of each fraction are buffer exchanged and analyzed with SDS-PAGE.

4. Selected fractions from the HIC capture are pooled for further purification. The pooled fractions are diafiltered into 50 mM Tris, pH 7.0 on a 5 kDa Minimate system. The concentrated and buffer exchanged SEG is then loaded over a Q Sepharose Fast Flow column and the load flow is collected.

5. The LFT from the AEX void chromatography step is then ultrafiltered on a 25 kDa Minimate system for volume reduction prior to gel filtration.
6. The retentate from the ultrafiltration is 0.45 pm filtered and then loaded onto a Sephacryl S-200 HR gel filtration column equilibrated with IX PBS, pH 7.4.
7. All peaks are collected in fractions and analyzed with SDS-PAGE and silver staining. Selected fractions are pooled, 0.22 pm filtered, and samples transferred to Quality Control for analysis.

The references to amino acid sequences of SEG-SEU are incorporated by reference and their references in entirety as follows: SEG (Baba, T. et al, Lancet 359, 1819-1827 (2002)); SEG (Jarraud, S et al, J. Immunol. 166: 669-677 (2001)); SEH (Omoe, K. et al, J. Clin. Microbiol. 40: 857-862 (2002)); SEI (Kuroda, M. et al, Lancet 357:1225-1240 (2001)); SEJ (Zhang S. et al, FEMS Microbiol. Lett. 168:227-233 (1998)); SEK (Baba T., et al, Lancet 359: 1819-1827 (2002)); SEL (Kuroda M. et al, Lancet 357: 1225-1240 (2001)); SEM (Kuroda M. et al, Lancet 357: 1225-1240 (2001)); SEN (Jarraud S et al, J. Immunol. 166: 669-677 (2001)); SEO (Jarraud S et al, J. Immunol. 166: 669-677 (2001)); γ/ent 1 (Jarraud S et al., J. Immunol. 166: 669-677 (2001)); γ/ent 2 (Jarraud S et al, J. Immunol. 166: 669-677 (2001)); SEP (Kuroda M. et al, Lancet 357: 1225-1240 (2001); SEQ (Lindsay, J A et al, Mol. Microbiol. 29: 527-543 (1998)); SER Omoe K et al., ACCESSION BAC97795; SEU (Letertre C et al, J. Appl. Microbiol. 95: 38-43 (2003)).

Thymidine Incorporation Assay

In triplicate, C57BL/6 and HLA-DQ8 splenocytes ($2 \times 10^5$ cells/well) were seeded in 96-well round-bottom tissue culture plates (Becton Dickinson) in complete RPMI. For some experiments, T cells were isolated using the Cellect-plus mouse T-cell kit (Biotex, Alberta, Canada). Splenocytes were cultured 72 hrs (37° C., 5% CO2 and humidity) in 200 µl total volume with medium alone, various concentrations of SEA, SEB, SEG, and SEI (0.001-1000 ng/ml) and with Concanavalin A (1.25 µg/ml) (Sigma Aldrich). At 68 hrs incubation, cells were pulsed with 1 µCi/well [$^3$H] thymidine (Perkin Elmer); radioactivity was measured 4 hours later as described previously. EC50 for each superantigen was derived from the data using the GraphPad program. (Kohler, P. L., (2012). PLoS ONE, 7(7), e41157).

CFSE Proliferation Assay

T cell proliferation was evaluated using carboxyfluorescein succinimidyl ester (CFSE) staining (Molecular Probes, Life Technologies). In short, C57BL/6 and HLA-DQ8 splenocytes ($2 \times 10^5$ cells/well) were seeded in 96-well round-bottom tissue culture plates (Becton Dickinson) in complete RPMI. Splenocytes were cultured 72 hrs (37° C., 5% CO2 and humidity) in 200 µl total volume with medium alone, various concentrations of SEA, SEB, SEG, and SEI (0.001-1000 ng/ml) and with Concanavalin A (1 µg/ml) (Sigma Aldrich). After 3 days, cells were processed for extracellular staining according to manufacturer recommendations (BioLegend). Cells were blocked with FC-block (BD Biosciences), and subsequently stained with anti-mouse CD3 APC-Cy7 (clone 17A2; Tonbo Biosciences, Irvine, Calif.), anti-mouse CD8 BV650 (clone 53.6-7; eBioscience, San Diego, Calif.), anti-mouse CD4 BV800 (clone RM4-5; Biolegend, San Diego, Calif.), and Ghost Dye Violet 450 (Tonbo Biosciences). (Quah, B J C et al., J. Vis. Exp. (44), e2259, doi: 10.3791/2259 (2010)).

Tumor Vaccination Experiments

For vaccination experiments, mice were injected with $1 \times 10^6$ irradiated (15,000 rads) B16-F10 melanoma cells intraperitoneally (i.p.) in 100 µl PBS. On day 6 and day 10, groups of 10 mice received 100 µl injections i.p. of SEG (50 µg), SEI (75 rig), and SEG&SEI (50 µg each) along with controls receiving no treatment, vaccination only and SEG&SEI only served as controls. Mice were challenged 13 days after vaccination with $2.5 \times 10^5$ B16-F10 cells. Mice were continuously evaluated and sacrificed when moribund. For treatment of established tumor, C57BL/6 female mice were injected i.p. with $1 \times 10^4$ live B16F10 melanoma cells on day 0 and subsequently injected with 50 µg each of SEA and SEB on day +7 and day +9. Mice were evaluated on a daily basis and sacrificed when moribund.

Tumor Outgrowth Experiment

Mice were implanted with $1 \times 10^4$ B16-F10 melanoma cells or LLC cells intraperitoneally (i.p.) in 100 µl PBS. Groups of 10 mice received 100 µl injections i.p. of SEG&SEI (50 µg each) on day 3 and 6 post implant. Including control mice receiving no treatment. Mice were continuously evaluated and sacrificed when moribund.

Cytotoxicity Assays

Cytotoxicity was measured by LDH (Thermo) and propidium iodide (PI) staining (Tonbo). Spleens were harvested, processed into a single cell suspension and RBCs were lysed. CD4+ and CD8+ lymphocytes were isolated using STEMCELL Technologies EasySep™ kit. Lymphocytes were co-cultured with B16-F10 cells for 12 hours at 37° C. with 5% $CO_2$ in cDMEM and stained with propidium iodide and reported as % B16-F10 PI positive. Statistics: one-way ANOVA w/Bonferroni post test.

Cytokine CBA Analysis

Spleens were harvested from naive C57BL/6 and HLA-DQ8 mice, processed into single cell suspensions, plated at $1 \times 10^6$ cells per well and simulated with superantigens. Supernatant was collected at 24 and 72 hrs post stimulation and cytokines were quantified using BioLegend's CBATh Cytokine kit. TH cytokines or the CBA kit (BD Biosciences)

Flow Cytometry

Samples were analyzed using a BD LSRII flow cytometer in the North Dakota Flow Cytometry and Cell Sorting (ND FCCS) Core. Data was further analyzed using FlowJo software (Ashland, Oreg.)

Data Analysis

Representative results are reported throughout the manuscript. One-way analysis of variance with Bonferroni's post test was performed on thymidine incorporation analysis, t-cell proliferation, cytotoxicity assays, and cytokine analysis. The Mantel-Cox Test was used to evaluate survival data. Statistical analysis was performed using GraphPad Prism software version 5.0d (GraphPad Software, Inc., La Jolla, Calif.).

Results

Challenge of C57BL/6 and DQ Transgenic Mice with Live LLC Cells Induces Comparable Survival We first determined whether the live LLC cells indigenous to the C57BL6 mice could be lethal to both C57BL/6 and DQ tg mice. Accordingly, we injected $2.5 \times 10^5$ LLC cell i.p. into C57BL/6 and DQ tg mice. Results show that this dose was lethal in median of 25-30 days in both strains of mice. Surprisingly, the DQ transgenic mice actually showed a slightly prolonged survival relative to C57BL/6 mice (FIG. 1). Hence it appears that DQ mice do not abnormally reject the LLC. This was confirmed in mixed lymphocyte studies wherein the DQ splenocytes showed no significant reactivity against C57BL/6 splenocytes.

Figure 2:
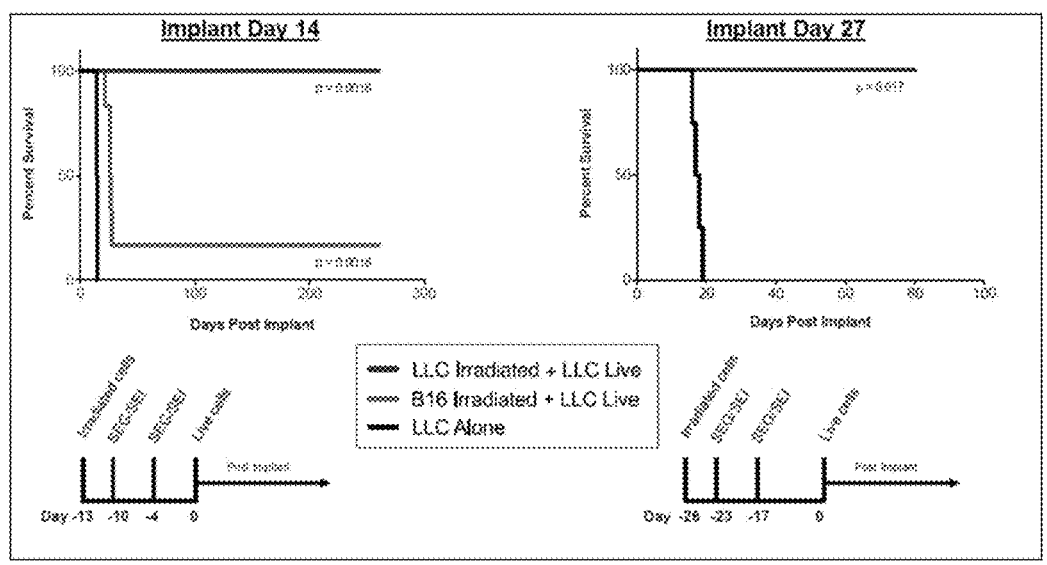

Attenuation of Lewis Lung Carcinoma Tumorigenesis in DQ Mice by Irradiated Tumor Cell Vaccination Followed by SEG or SEI Next, we determined whether SEG and SEI could augment the anti-tumor effect of tumor cell vaccination with irradiated tumor cells. DQ mice were vaccinated with irradiated B16F10 LLC cells on day −13 and subsequently treated with SEG or SEI (50 n i.p. on days −7 or day −3). Control mice received SEG/SEI without irradiated tumor cell vaccination. All mice were challenged with $2.5 \times 10^5$ viable B16F10 cells on day 0. One hundred percent of mice receiving irradiated tumor cell vaccination followed by SEG, SEI or SEG/SEI on days −7 and −3 followed by viable tumor cells on day 0 survived for 200 days significantly longer than mice treated with irradiated tumor cell vaccination alone, viable tumor cells alone or SEG and SEI as the sole treatment (FIG. 2). Similarly, 100% of DQ mice immunized with irradiated LLC cells on day −26 and immunized with SEG and SEI on day −23 and −17 but challenged with live tumor cells on day 0 showed survival of 100 days from the day of live tumor challenge relative to controls (FIG. 2). Thus, irradiated tumor cell vaccination plus SEG/SEI appeared to protect the host from outgrowth of a lethal dose of LLC. Notably, immunization with irradiated B16 melanoma was significantly less effective than irradiated LLC in protecting mice from lethal challenge with live LLC cells (FIG. 2). These mice demonstrated no significant acute or chronic toxicity such as toxic shock, weight loss, cachexia noted previously with SEB and SPEA usage in humanized MHCII tg mice.

Anti-Tumor Effect of SEG/SEI in DQ8 Against Established LLC in DQ8 Mice

Figure 3:
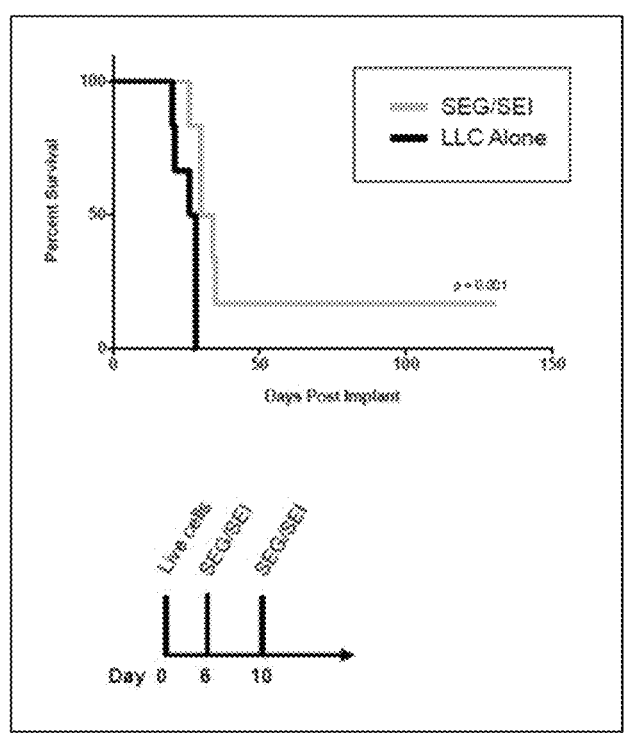

Next, we determined whether SEG/SEI could exert an antitumor response against established LLC in transgenic DQ mice. LLC tumor was implanted i.p. on day 0 and SEG and SEI (50 μg of each) was administered i.p. on days +6 and +9. Results shown in FIG. 3 demonstrate that the mice treated with SEG/SEI after live tumor challenge survived longer than untreated mice challenged with live LLC cells alone. Therefore, SEG/SEI appears to significantly prolong the survival of mice bearing LLC in HLA-DQ8 mice. These mice demonstrated no significant acute or chronic toxicity such as toxic shock, weight loss, cachexia noted previously with SEB and SPEA usage in humanized MHCII tg mice.

Anti-Tumor Effect of SEG/SEI in DQ8 Mice Against Established B16F10 Melanoma

Figure 4:
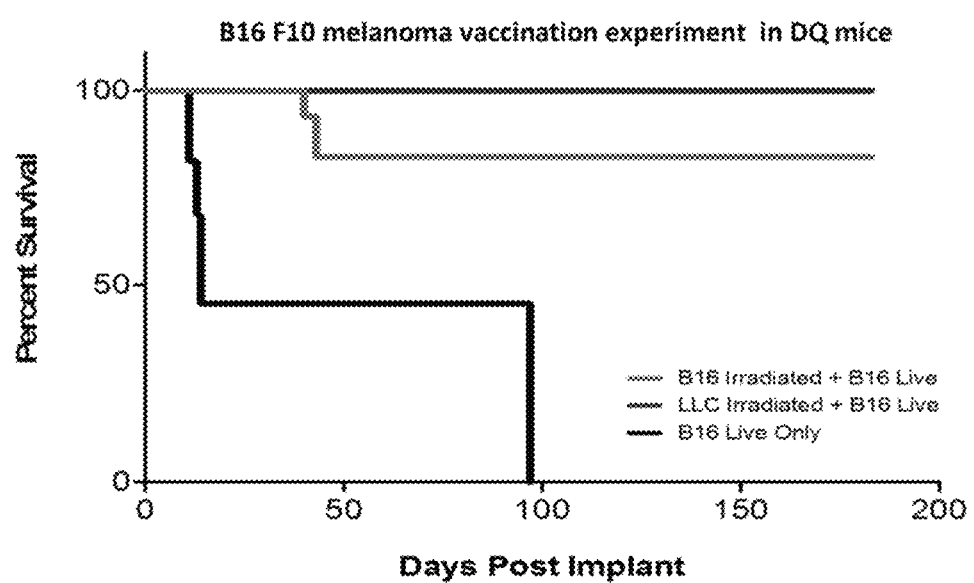

We wished to determine whether SEG/SEI could exert an antitumor response against de novo B16F10 melanomas in transgenic HLA-DQ mice. DQ mice were vaccinated with irradiated B16F10 melanoma cells on day −13 and subsequently treated with SEG or SEI individually or SEG together with SEI (50 μg i.p. on days −7 or day −3). Control mice received SEG/SEI without irradiated tumor cell vaccination. All mice were challenged with $2.5 \times 10^5$ viable B16F10 cells on day 0. Mice receiving irradiated tumor cell vaccination followed by SEG, SEI or SEG/SEI on days −7 and −3 followed by viable tumor cells on day 0 survived significantly longer than mice treated with irradiated tumor cell vaccination alone (FIG. 4). These mice demonstrated no significant acute or chronic toxicity such as toxic shock, weight loss, cachexia noted previously with SEB and SPEA usage in humanized MHCII tg mice.

Figure 5:
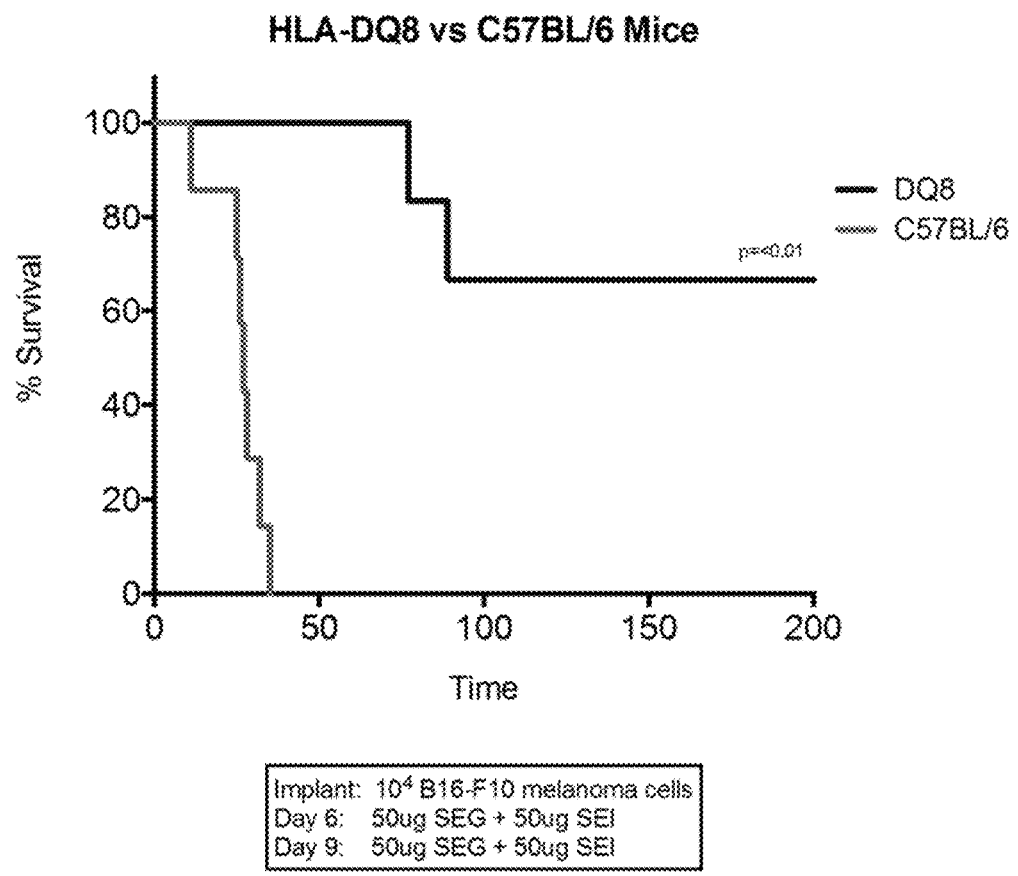

To test the effect of SEG and SEI versus established B16F10 tumor we implanted live B16F10 melanoma on day 0 and SEG/SEI (50 μg of each) were administered i.p. on days +6 and +9. Two hundred days after tumor implantation 65% of the DQ8 mice receiving SEG/SEI were still alive compared to 30% of the untreated mice. Therefore, SEG/SEI appears to significantly prolong the survival of mice bearing B16F10 melanoma in HLA-DQ8 mice relative to C57BL/6 mice (p=0.01) (FIG. 5). These mice demonstrated no significant acute or chronic toxicity such as toxic shock, weight loss, cachexia noted previously with SEB and SPEA usage in humanized MHCII tg mice.

Figure 6A:
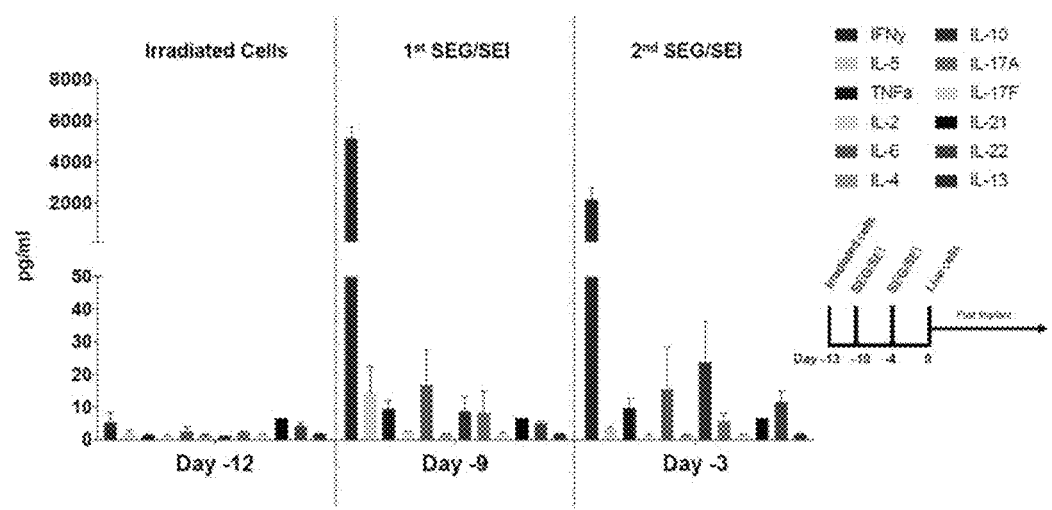
Figure 6B:
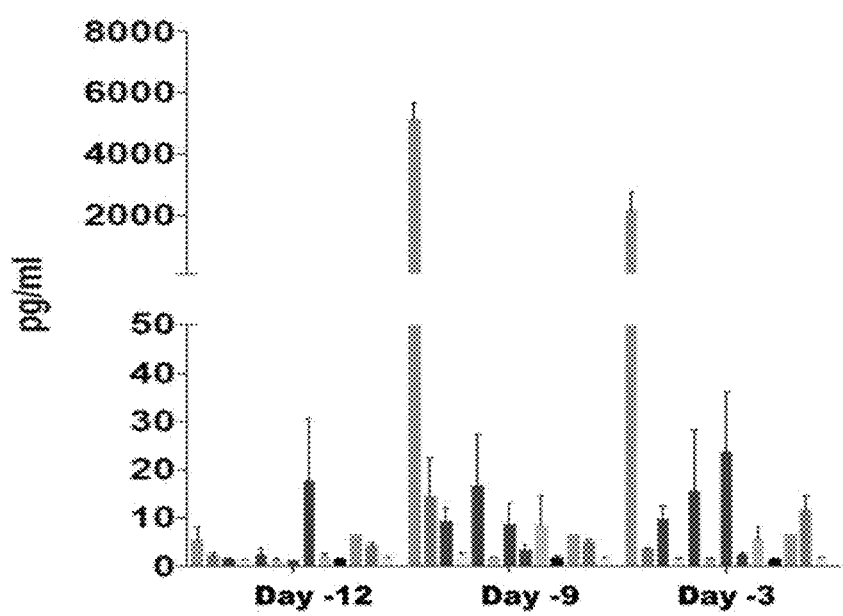

Serum Cytokine Response in DQ Mice During Vaccination with Irradiated LLC Cells and SEG/SEI Serum cytokines were obtained at various intervals after vaccination with irradiated LLC cells or B16F10 melanoma cells plus SEG/SEI on days −6 and −9 with live cell inoculation on day 0. One day after delivery of irradiated tumor cells cytokine levels were at baseline levels. However, on day −7, 1 day after the first SEG/SEI immunization both groups of mice exhibited a dramatic surge of IFNγ reaching levels 3000 fold above baseline. One day after the second SEG/SEI immunization on day −10, IFNγ levels still remained 800 fold above baseline (FIG. 6). This surge was unattended by a comparable increase in toxicity inducing cytokines IL-2 or TNFα levels. Nor did these mice show any signs of acute, chronic or systemic toxicity.

Superantigens are known to activate serum cytokines notably of the TH-1 subgroup to include INFγ, TNFα and IL-2. In most instances the augmentation of the INFγ is accompanied by a parallel increase in the TNFα and IL-2. This accounts for the toxicity of the SAgs such as SEB in HLA-DR transgenic mice. In contrast we noted that doses of two SAgs SEG and SEI 10-12 fold above the lethal dose of SEB (5 μg) did not induce toxic shock and led to the significant tumoricidal effects. In fact, the cytokine profiles for SEG/SEI included a massive spike of INFγ associated with minimal surges of TNFα and IL2. After SEG/SEI immunization, the ratios of the IFNγ to TNFα and IL2 were 6000/10 and 6000/2 in HLA-DQ8 mice versus 1800/150 and 1800/4000 following SEB immunization in HLA-DR mice (Tilahun A Y Mediators of Inflammation doi.org/10.1155/2014/468285; Rajagopalan G et al., Tissue Antigens 71:135-145 (2007)); Sriskandan, S., M J. Infect. Dis. 184: 166-173. (2001). SEG/SEI presented from a DQ8 platform induce an anti-tumor effect with less toxicity than SEB despite a 10 fold higher dose of each. The cytokine ratios in the SEG/SEI treated mice show that a strong surge of IFNγ is a major contributor to the anti-tumor effect while the minimal toxicity may be ascribed to low levels of TNFα and IL-2.

Figure 7:
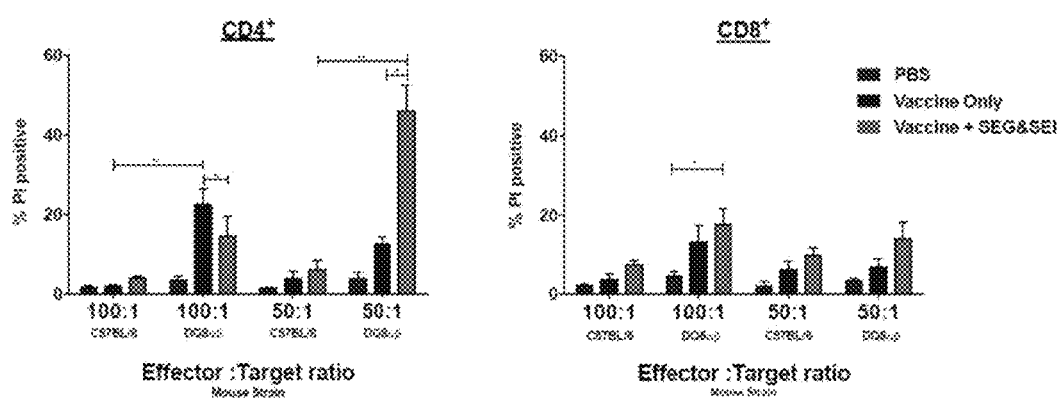

Cytotoxic T Lymphocyte Response of DQ8 and C57BL/6 Mice to Vaccination with Irradiated B16F10 Melanoma Cells and SEG/SEI B16F10 melanoma was implanted i.p. in DQ8 and C57Bl/6 mice which were then were immunized with SEG/SEI (50 μs of each) i.p. on days −7 and −9. Three days later splenocytes were evaluated for cytotoxicity against B16 melanoma cells. Results show that CD4+ T cell mediated cytotoxicity was significantly increased in DQ8 mice (FIG. 7). This surge in CD4+-mediated cytotoxicity correlated with the surge in serum levels of INFγ noted above at this stage of immunization as shown in FIG. 6.

Figure 8:
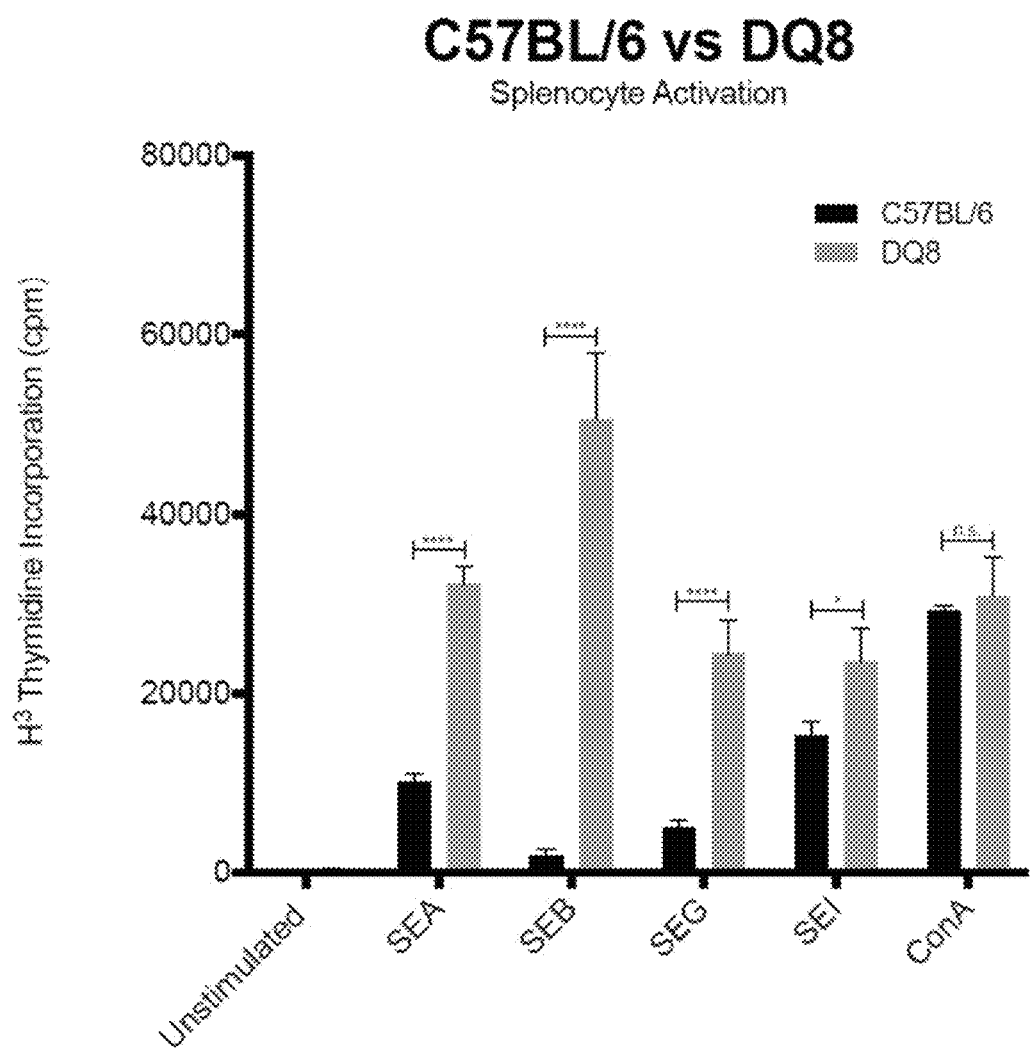

Comparison of T Cell Proliferation in Splenocytes from C57Bl/6 or DQ8 Mice in Response to SEA, SEB, SEG and SEI Next we compared T cell proliferation in response to SEG, SEI, SEB and SEA in splenocytes derived from C57Bl/6 mice and transgenic HLA-DQ8 mice. Splenocytes from HLA-DQ8 mice exhibited an exaggerated T cell proliferation in response to all 4 superantigens with peak amplitudes 2-4 fold greater than corresponding splenocytes from C57Bl/6 mice. Thus splenocytes from HLA-DQ8 mice are more reactive than those from C57Bl/6 mice in T cell activation by all 4 SEs (FIG. 8).

The T cell phenotype from DQ8+ and C57BL/6 mice after stimulation with SEG and SEI was predominantly CD8+ with PD1+, CTLA4+ and CXCR3+ expression whereas the C57BL/6 mice showed an ascendant CD4+ phenotype and significantly lower expression of PD1+, CTLA4+ and CXCR3+ on CD8+ T cells.

Discussion

Surprisingly, this study shows that SEG and SEI exhibit significant anti-tumor effects in MHC-DQ8 tg mice versus the Lewis lung carcinoma and B16F10 melanoma without toxicity. The anti-tumor effect of SEG and SEI in DQ tg mice is associated with a dramatic increase in serum levels of IFNγ devoid of a spike in TNFα levels. Serum levels of TNFα never exceeded the 40 ng/ml level that was associated with Grade 3-4 toxicity in humans after administration of unmodified SEA (Alpaugh supra (1998)). Nor did they rise to lethal levels of 600 or 1000 pg/ml in DQ8 transgenic mice after injection of SPEA and SEB respectively (Welcher et al., supra (2002); Tillahun supra (2014)); The ratio of serum levels of these agents ranged from 800-3000:1. The basis of the anti-tumor effect of SEG and SEI in MHC-DQ8 mice is the presentation of SEG and SEI to T cells in DQ8 tg mice by MHCII DQ8 molecules which leads to a selective surge in IFNγ devoid of a parallel spike in TNFα levels. This effect could not be predicted from the cytokine profile of SEI in humans which shows the highest levels of all SAgs in both INFγ and TNFα (Terman et al., Front. Cell Infect. Micro. 3: doi: 10.3389/fcimb.2013.00038). Nor could it be assumed from the cytokine profile of SEG which exhibits the lowest levels IFNγ and TNFα of all SAgs. Surprisingly, when used together in the DQ8 humanized mice SEI's high IFNγ production is maintained while its TNFα production is suppressed. This effect could not have been foretold from the behavior of other SAgs such as SEB and SPEA in humanized MHCII mice. These agents induced toxic shock in humanized MHCII mice in doses 10 fold lower than SEG and SEI associated with high serum levels of both IFNγ and TNFα in ratios of 0.6 and 3:1 respectively. Hence, the combination of SEG and SEI in MHC DQ mice leads to an IFNγ surge that is highly advantageous for anti-tumor activity devoid of a parallel spike in TNFα the key cytokine mediator of SAg-induced toxic shock.

In association with the high IFNγ:TNFα ratio in DQ8 mice vaccinated with SEG and SEI these mice also displayed a 3 fold increase in CD4+ mediated cytotoxicity versus B16F10 melanoma cells. This surge in CD4+ cytotoxicity correlates with the spike in IFNγ. Although it is well established that the CD4+ cells are able to exert anti-tumor responses, there are no reports of unmodified superantigens inducing a selective IFNγ surge of 4000-6000 pg/ml without also triggering toxic levels of TNFα exceeding 40 pg/ml. The acute onset of lethal shock in humanized MHCII mice treated with SEB and SPEA indicates that the toxic effects of TNFα can preclude recognition of any anti-tumor effect (Sriskandan, S., M J. Infect. Dis. 184: 166-173. (2001); Llewelyn Metal., J Immunol. 172:1719-26 (2004); Welcher et al., J. Infect. Dis. 186:501-10 (2002)). Although, it is known that SAgs can produce differential cytokine profiles when presented by different MHCII molecules, the selective INFγ surge unaccompanied by TNFα and IL-2 produced by a combination of SEG and SEI is unprecedented in the literature. Indeed, the discovery of a combination of biologics (SEG and SEI) exhibiting a selective burst of a tumor killing cytokine such as INFγ in a humanized MHCII model is unexpected, novel and unobvious from the prior art.

The antitumor responses to SEG and SEI in DQ8 tg mice exceed in scale the effects of SEG and SEI against the same tumors in C57BL/6 mice. This is not unexpected since the latter strain displays a genetic deletion in Vβ8.2 which is the natural TCR docking site for SEG. The lower cytotoxicity levels and cytokine profile after SEG stimulation in C57BL/6 mice reflects this deletion. In contrast humanized MHCII tg mice mimic humans in their high sensitivity to the toxic effects of superantigens. This is exemplified in the toxic shock responses to SEB and SPEA in humanized MHCII tg mice at doses that are normally well tolerated in C57BL/6 mice (Kominsky et al., Int. J. Cancer 94: 834-841 (2001); Sriskandan et al., J. Infect. Dis. 184: 166-173 (2001); Llewelyn et al., J. Immunol. 172:1719-1726 (2004); Tilahun Mediators of Inflammation doi.org/10.1155/2014/468285; Rajagopalan et al., Tissue Antigens 71:135-145 (2007)). Anti-tumor and toxicity studies of superantigens such as SEG which depend on the Vβ8.2 linkage cannot be reliably assessed in C57BL/6 mice because Vβ8.2 the major docking site of SEG is deleted in these mice. Hence, the study of Kominsky showing that SEB and SEA were effective in killing melanoma without toxicity in C57BL/6 mice cannot be translated to humans. Indeed, when SEB was used in humanized MHCII mice and humans with intact Vβ8.2 it induced toxic shock and stage 4 cardiopulmonary toxicity respectively (Young et al., Am. J. Med. 75: 278-286 (1983); Llewelyn Metal., J. Immunol. 172:1719-1726 (2004)).

Therapeutic MHCII-DQ8-SEG and SEI Expressed on Living Cells, Irradiated Cells or Non-Viable Particles for Delivery to Tumor Bearing Hosts Having shown that SEG-SEI presented from a DQ8 platform induce a robust anti-tumor response associated with a cytokine profile with IFNγ/TNFα ratio exceeding 800:1, the inventors now contemplate that SEG and SEI can be delivered to a host conjugated to a DQ8 scaffold on a living cell or irradiated cell or nanoparticle. MHC-DQ8 are transmembrane proteins and therefore can be produced recombinantly in live cells such as tumor cells and be expected to localize in the cell membrane. In this example live cells including but not limited to tumor cells, fibroblasts, K562 cells and erythroid stem cells (discussed below) are transduced with lentiviral vector comprising the powerful EF1 promoter driving construction of the DQ8 alpha or beta chains as polycistronic construct or as two individual genes. Tumor cells are preferred for this usage but all cells used for this purpose should not express either native or induced MHCII molecules that could compete for binding of the SEG and SEI superantigens. After cell transduction the recombinant DQ8 alpha and beta chains are membrane bound. SEG and SEI in in PBS are incubated with these cell for 1-24 hours at 37° C. and bind avidly to the cell bound DQ8 receptors. They may also be covalently linked to these receptors using bifunctional linkers described below. If transduced tumor cells are used they are irradiated with 15000 rads in vitro before addition of SEG and SEI. The final cells are administered parenterally preferably by intravenous injection or infusion in doses of 1 to $15\times10^7$ every 2-7 days. This ensures that the SEG and SEI are preferentially bound to the MHC-DQ8 expressing cells rather than to host MHCII receptors for presentation to host T cells after in vivo administration.

To express DQ8 alpha and beta chains on enucleated RBCs we incorporated them into a β-globin lentiviral vector under control of the powerful Locus Control Region and used this vector to transduce hematopoietic stem cells. The latter transduced cells are differentiated in vitro into erythroid progenitor cells and reticulocytes which express DQ8 alpha and beta chains on their surface. Erythrocytes expressing MHC-DQ8 alpha and beta chains are incubated with molar excess of SEG and SEI as above with nucleated cells, then washed three times and administered as described below. Enucleated cells do not possess MHCII molecules and therefore can be used in native form after transduction with recombinant MHCII-DQ8 alpha and beta chains.

Preparation of 4T1 Tumor Cells Expressing DQ8 Alpha and Beta Chains

Figure 9A:
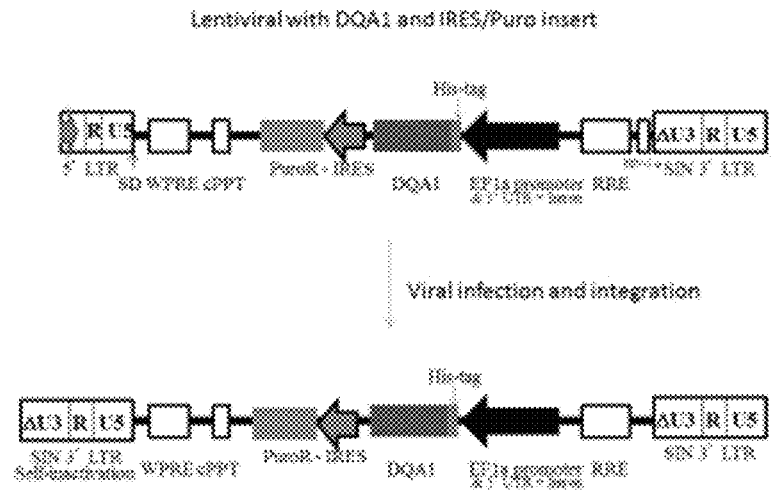
Figure 9B:
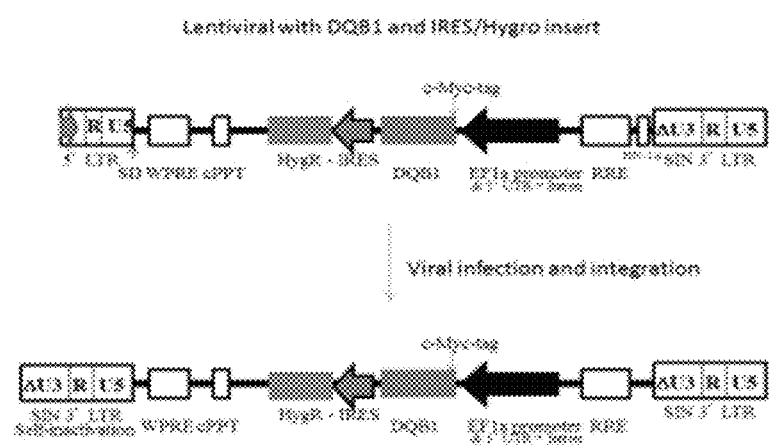
Figure 9C:
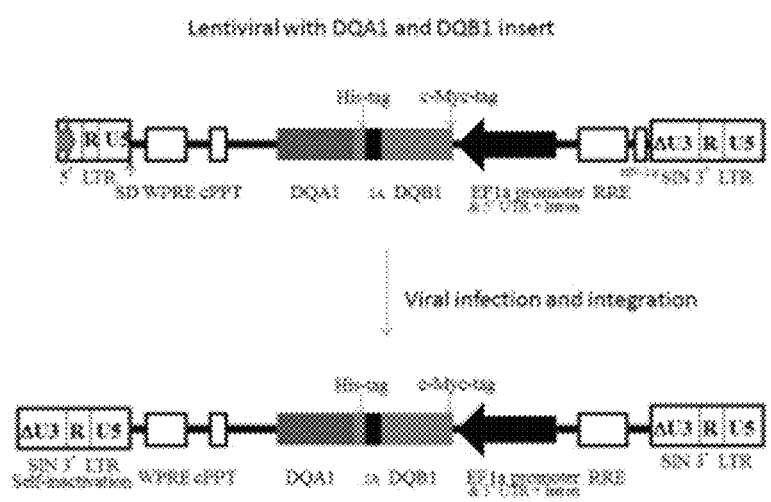
Figure 10A:
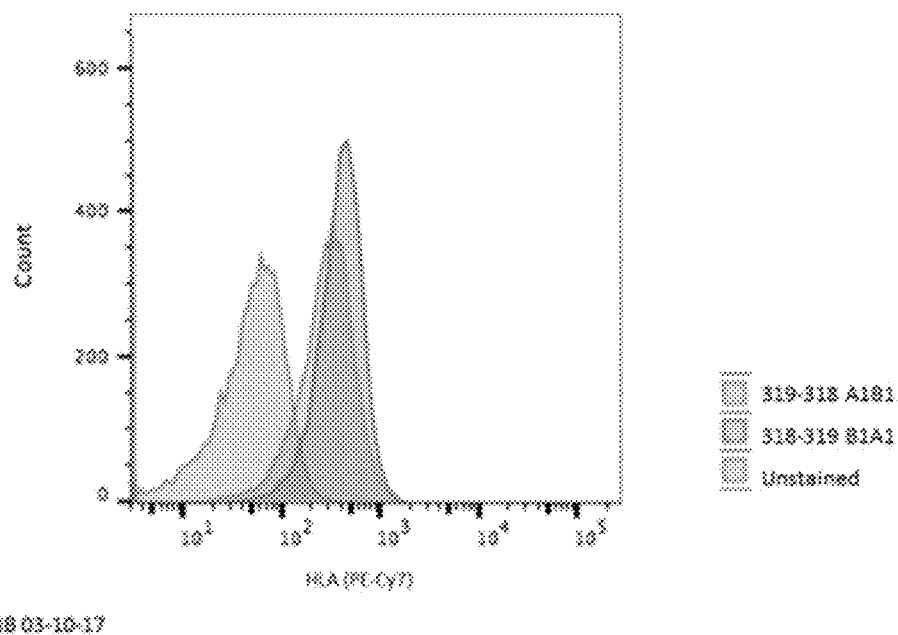
Figure 10B:
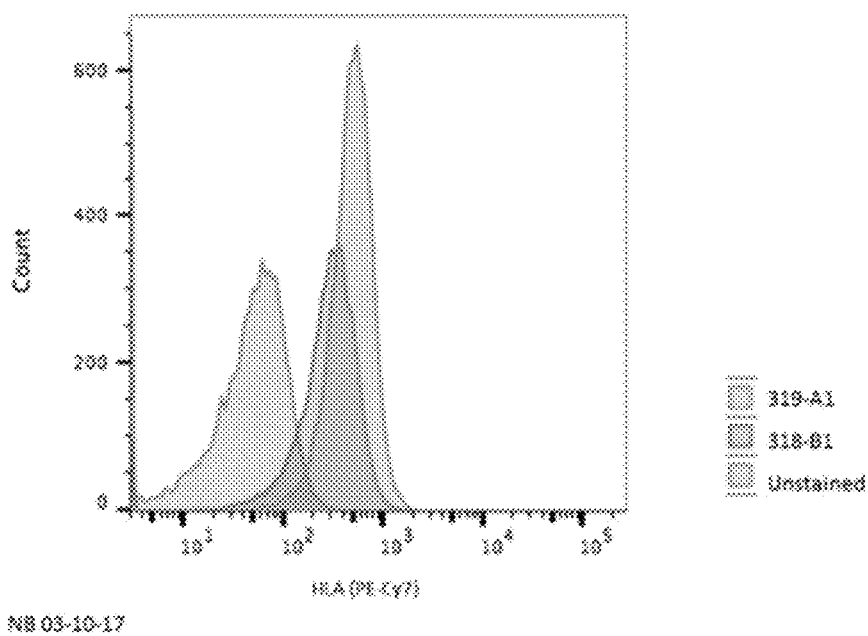
Figure 11:
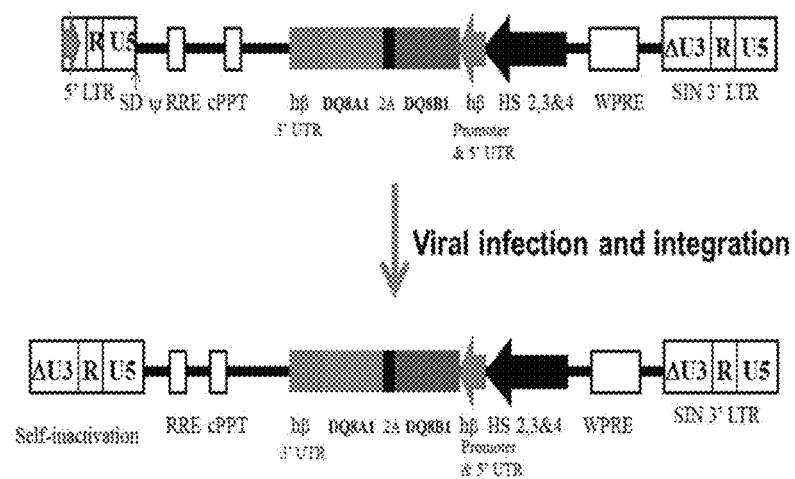

DQ8A1 alpha chain cDNA with flanking sequences of 20 base pairs to EF1 alpha (on the 5' end) and IRES (on the 3' end) was cloned into a lentiviral vector with a puromycin resistant marker. Vector diagrams are given in FIG. 9. The DQ8β1 beta chain cDNA is subcloned into another lentiviral vector with hygromycin marker. To generate the polycistronic DQβ1 and DQA1 in a lentiviral vector we used one forward oligoprimer to DQB1 plus 20 nucleotides with homology to EF1 alpha and one reverse primer to DQβ1 plus part of P2A linker for PCR. PCR-amplified DQβ1 cDNA plus 20 bp to EF1 alpha at 5' plus part of P2A at 3' was therefore prepared. The new DQA1 cDNA was also amplified by PCR with a forward primer to the P2A linker and another reverse primer to DQA1 plus 20 nucleotides to IRES. The PCR amplified new cDNA DQβ1 and DQA1 cDNAs were extracted from agarose gel. The full-length DQβ1-P2A-DQA1 cDNA was synthesized by overlap PCR from the purified DQA1 and DQβ1 with the same forward primer to DQβ1 and the same reverse primer to DQA1. 4T1 murine mammary carcinoma cells were infected for 12 hours with virus at moi 10 (10:1 virus to cell ratio). The hygromycin resistant 4T1 cells were infected with virus moi 10. The double positive hygromycin and puromycin resistant 4T1 cells were selected and frozen for future study. To generate polycistronic DQβ1-DQA1 positive 4T1 we used 30 moi (30 virus:1 cell ratio) in 4T1 cells. The localization of MHC-DQ alpha and beta chains on the tumor cell surface was confirmed by flow cytometry (FIG. 10 A,B). For loading SEG and SEI, MHC-DQ expressing cells are irradiated with 15000R and then loaded by incubating SEG and SEI 10-50 µg per $10^6$ MHC-DQ8 expressing cells for 1-24 hours at 37° C. The cells are washed three times remove excess SEG and SEG and administered parenterally by infusion or injection in doses of $1-15 \times 10^6$ cells every 2-3 days for up to 6 treatments. This ensures that the SEG and SEI are preferentially bound to the MHC-DQ8 for presentation to host T cells when these cells are administered in vivo. The cDNA and amino acid sequences of DQ8 alpha and beta chains are depicted below.

Production of human tumor cells expressing MHC-DQ8-SEG and SEI is accomplished by the above protocol with slight variations that create no undue burden on the skilled scientist. These tumor cells may be autologous or allogeneic to the patient. Methods for culture, multiplication and harvesting of such cells for transduction with MHC-DQ and affixation of SEG and SEI are well established in the literature. These cells are administered parenterally by infusion or injection in doses of $1-15 \times 10^6$ cells every 2-3 days for up to 6 treatments. as described in the clinical trial in Example 1.

```
(SEQ ID NOS: 1 and 2)
His-tag
ATG-CATCACcatCACCATCAC

DQ8A1 cDNA
atcc 61  taaacaaagc tctgctgctg ggggccctcg ctctgaccac cgtgatgagc ccctgtggag 121  gtgaagacat tgtggctgac cacgttgcct cttgtggtgt aaacttgtac cagttttacg 181  gtccctctgg ccagtacacc catgaatttg atggagatga gcagttctac gtggacctgg 241  agaggaagga gactgcctgg cggtggcctg agttcagcaa atttggaggt tttgacccgc 301  agggtgcact gagaaacatg gctgtggcaa aacacaactt gaacatcatg attaaacgct 361  acaactctac cgctgctacc aatgaggttc ctgaggtcac agtgttttcc aagtctcccg 421  tgacactggg tcagcccaac accctcattt gtcttgtgga caacatcttt cctcctgtgg 481  tcaacatcac atggctgagc aatgggcagt cagtcacaga aggtgtttct gagaccagct 541  tcctctccaa gagtgatcat tccttcttca agatcagtta cctcaccttc ctccctIctg 601  ctgatgagat ttatgactgc aaggtggagc actggggcct ggaccagcct cttctgaaac 661  actgggagcc tgagattcca gccctatgt cagagctcac agagactgtg gtctgtgccc 721  tggggttgtc tgtgggcctc atgggcattg tggtgggcac tgtcttcatc atccaaggcc 781  tgcgttcagt tggtgcttcc agacaccaag ggccattgtg a
```

```
(SEQ ID NOS: 3-5)
c-myc tag
gcc acc ATG GAA CAA AAA CTT ATT TCT GAA GAA

DQB1-cDNA
tct 61  tggaagaagg attgcggat ccctggaggc cttcgggtag caactgtgac cttgatgctg 121  gcgatgctga gcaccccggt ggctgagggc agagactctc ccgaggattt cgtgtaccag 181  tttaagggca tgtgctactt caccaacggg acggagcgcg tgcgtcttgt gaccagatac
```

-continued

```
241  atctataacc gagaggagta cgcacgcttc gacagcgacg tggggggtgta tcgggcggtg 301  acgccgctgg ggccgcctgc cgccgagtac tggaacagcc agaaggaagt cctggagagg 361  acccgggcgg agttggacac ggtgtgcaga cacaactacc agttggagct ccgcacgacc 421  ttgcagcggc gagtggagcc cacagtgacc atctccccat ccaggacaga ggccctcaac 481  caccacaacc tgctggtctg ctcagtgaca gatttctatc cagcccagat caaagtccgg 541  tggtttcgga atgaccagga ggagacaact ggcgttgtgt ccaccccct tattaggaac 601  ggtgactgga ccttccagat cctggtgatg ctggaaatga ctccccagcg tggagacgtc 661  tacacctgcc acgtggagca ccccagcctc cagaacccca tcaccgtgga gtggcgggct 721  cagtctgaat ctgcccagag caagatgctg agtggcattg gaggcttcgt gctggggctg 781  atcttcctcg ggctgggcct tattatccat cacaggagtc agaaagggct cctgcac
```

P2A-sequence
GGAAGCGGAGCTACTAACTTCAGCCTGCTGAAGCAGGCTGGAG

ACGTGGAGGAGAACCCTGGACCT (SEQ ID NO: 6)
Amino acid sequence of translated polycistronic DQ8 alpha and beta chains
ATMEQKLISEESWKKALRIPGGLRVATVTLMLAMLSTPVAEGRDSPEDFV

YQFKGMCYFTNGTERVRLVTRYIYNREEYARFDSDVGVYRAVTPLGPPAA

EYWNSQKEVLERTRAELDTVCRHNYQLELRTTLQRRVEPTVTISPSRTEA

LNHHNLLVCSVTDFYPAQIKVRWFRNDQEETTGVVSTPLIRNGDQTFQIL

VMLEMTPQRGDVYTCHVEHPSLQNPITVEWRAQSESAQSKMLSGIGGFVL

GLIFLGLGIIHHSQKGLLHGSGATNFSLLKQAGVEENPGPMHHHHHHI

LLNKALLLGALALTTVMSPCGEDIVADHASCGVNLYQFYFPSFQFYTHEF

DFDEQFHVDLERKETAWRWPEFSKFGGDPQFALRNMAVAKHLNIMIKRYN

STAATNEVPEVTVFSKSPVTLGQPNTLICLVDNIFPPVVNITWLSNGQSV

TEGVSETSGSKSDHSFFKISYLTFLPSADEIYDCKVEHWGLDQPLLKHWE

PEIPAPMSELTETVVCALGLSVGLMGIVVGTVFIIQGLRSVGASRHQGPL

Testing Recombinant 4T1-DQ8 Cells Loaded Ex Vivo with SEG and SEI in Mice with the 4T1 Mammary Tumor Metastases The protocol for testing recombinant 4T1-DQ8 cells loaded ex vivo with SEG and SEI against established 4T1 mammary tumors is provided below.

| Effect of 4T1-DQ-SEG cells on established 4T mammary carcinoma | | | |
|---|---|---|---|
| | Gp 1: 6 BalbC | Gp2: 6 BalbC | Gp3: 6 BalbC |
| Day 0 | Implant $5 \times 10^4$ non-irradiated 4T1 cells in 0.1 ml DMEM subcut | Implant $5 \times 10^4$ non-irradiated 4T1 cells in 0.1 ml DMEM subcut | Implant $5 \times 10^4$ non-irradiated 4T1 cells in 0.1 ml DMEM subcut |
| Day 4 | Inject $10^6$ irradiated 4T1 cells* i.p. | Inject $10^4$ irradiated 4T1 cells* i.p. | |
| Day 10 or when tumor reach 0.5 mm in diameter | Inject $10^6$ irradiated 4T1-DQ-SEG-SEI cells i.p. then Q3 days for 3 doses | | |

Methods:
Mice: BalbC 8 weeks old females
*4T1 cell radiation dose: 15000 rads
4T1-DQ cells are incubated with SEG-SEI (10ug each)/$10^6$ tumor cells for 1 hour at 37° C. before i.p. injection
Count lung metastases on lung surface at end of experiment.

Mice in Group 1 above are injected with 4T1-DQ-SEG/SEI tumor cells on three separate occasions according to the above protocol. As shown below these mice showed fewer lung metastases than control mice not treated with 4T1-DQ-SEG/SEI tumor cells.

| Results | | | | |
|---|---|---|---|---|
| | Gp 1: 6 BalbC | Gp2: 6 BalbC | Gp3: 6 BalbC | Gp4: 6 BalbC |
| Lung Metastases | 1 | 6.75 | 3.25 | 9.25 |

Preparation of Human Erythrocytes Expressing MHCII-DQ8 Molecules
Beta Globin Lentiviral Vector Incorporating MHCII-DQ8 Alpha and/or Beta Chains The inventors contemplate that MHC-DQ8 alpha and/or beta chains can be recombinantly positioned on the surface of erythroid progenitors or erythroid precursors or mature erythrocytes by the methodology described below. Such MHC-DQ8 expressing erythroid cells are loaded with recombinant SEG and SEI and then infused into tumor bearing subjects. By using erythroid stem cells from various major blood groups the mature erythrocytes can be blood group matched to avoid blood group incompatibility reactions.

Nucleic acid sequences encoding DQ8A1 and DQ8B1 were obtained from Thermo Scientific. The full length lentiviral β-globin vector containing DQ8A1 and/or DQ8B1 transgene is modified from Levasseur et al., by substituting the DQ8A1 and/or DQ8B1 transgenes for the $B^{AS3}$-globin anti-sickling gene (Levasseur D N, Blood 102: 4312-4319 (2003)). In this vector, DQ8A1 and DQ8B1 transgenes are substituted for the coding region of the β-globin gene under control of the β-globin promoter (266 bp), the PstI 3' globin enhancer (260 bp) and a 375-bp RsaI fragment deletion of IVS2. (FIG. 11). The portion of the β-globin locus which includes the enhancer is found in the second intron of the β-globin gene as well as part of the third exon of β-globin and the enhancer located 3' to the human β-globin gene, poly A sequence and a β-globin Kozak sequence are retained for coding stabilization. Also retained in the vector are the locus control region (LCR) of DNase I hypersensitivity regions (HS2, 3 and 4). The β-globin promoter/enhancer (2.3-kb) along with DQ8A1 and DQ8B1 transgenes were subcloned into the pWPT-GFP vector replacing the EF1a promoter and green fluorescent protein (GFP). This self-inactivating (SIN) vector contains a deletion in the U3 region of the 3' long terminal repeat (LTR) from nucleotide 418 to nucleotide 18 that inhibits all transcription from the LTR. A biologic transgene replaces the coding region, exon 1 and 2, of the β-globin gene. The lentiviral-globin LTR contains in addition to the 3' globin enhancer, the β-globin promoter and the $\beta^{AS3}$ globin gene, a 3' SIN deletion, ψ packaging signal, splice donor and acceptor sites, Rev-responsive element, RRE, cPPT/CTS indicating central polypurine tract or DNA flap/central termination sequence and WPRE specifying woodchuck hepatitis vims post-transcriptional regulatory element. DNase 1 hypersensitive sited (HS) fragments 5' HS4 3, and 2 are amplified by polymerase chain reaction (PCR) from a 22-kb fragment of the LCR. Nucleotide coordinates from GenBank accession no. U01317 are: HS4 592-1545, HS3 3939-5151, and HS2 8013-9215. The entire HS4 3.2 β-globin gene construct is verified by sequencing.

Construction of the polycistronic genes construct using PTV1 2A sequences and fusion PCR was performed essentially as described (Levasseur D N et al., Blood 102:4312-9 (2003)). Briefly, the 3' end consisted of nucleotides (nt) from PTV1 P2A to form a 22-nt overlap with the bp 5' of the DQ8 alpha chain amplicon. Human DQ8 alpha chain cDNA (Thermo Scientific) was PCR amplified to append 2A nt sequences upstream of the DQ8 beta chain ATG. At the 3' end, the DQ8 beta chain stop codon was retained and Swa I restriction sites were added. After PCR the individual amplicons were gel purified and used in a fusion PCR along with primers DQ8 beta chain and DQ8alpha chain to produce an amplicon containing the polycistronic genes. The polycistronic gene was gel purified and cloned into the general cloning vector pBS-SK+ (Stratagene) using the SmaI restriction sites (enzymes from New England Biolabs) to produce pJS-AGP and sequenced for authenticity. Subsequently, the polycistron was subcloned into a SwaI site in the lentiviral vector to produce the DQ8A1-DQ8B1 polycistronic lentiviral vector which was sequenced for authenticity Production of β-Globin Lentiviral Vector Incorporating MHCII-DQ8 Alpha and Beta Chains β-globin lentiviral vector was produced by transient transfection into 293T cells (Levasseur D N et al., Blood 102: 4312-9 (2003)) with the following modifications (FIG. 11). A total of $2.5\times10^6$ 293T cells were seeded in 10-cm-diameter dishes containing Dulbecco modified Eagle medium (DMEM) with 10% fetal bovine serum (FBS) 24 hours prior to transfection. Forty micrograms plasmid DNA was used for transfection of one 10-cm dish. The DNA cocktail contained 5 μg envelope-coding plasmid pMDG, 15 μg of the packaging plasmid pCMVdR8.91 (which expresses Gag, Pol, Tat, and Rev) and 20 μg SIN transfer vector with genes of interest. Transfection medium was removed after 14 to 16 hours and replaced with DMEM/F12 without phenol red (Invitrogen, Carlsbad, Calif.) containing 2% FBS. Virus-containing supernatant was collected after an additional 24 hours, cellular debris are cleared by low-speed centrifugation, and filtered through a low protein-binding 0.22-μm polyether sulfone filter (Millipore, Bedford, Mass.). The virus was concentrated 1000-fold by one round of centrifugation at 26,000 rpm for 90 minutes at 8° C. using an SW-28 rotor (Beckman, Palo Alto, Calif.), resuspended into serum-free stem cell growth medium (SCGM) (Cellgenix, Freiburg, Germany) and incubated on ice for 4 hours before aliquot storages at −80° C. Virus titer was determined by infecting murine erythroleukemia (MEL) cells, with an EF1α-GFP control virus, and assaying GFP positive populations in the cultures by FACS analysis to determine the physical state of viral numbers.

Stem Cell Transduction with the β-Globin Vector Encoding MHCII-DQ Alpha and Beta Chains For stem cell transplantation studies in mice bone marrows are isolated from the femurs and tibias and Scal+ erythroid progenitor cells, purified by Stem Cell Technology mouse Scal+positive selection kit, catalogue #18756, and transfected with tumoricidal transgenes SEG and SEI as described above and resuspended at $1\times10^7$ cells/mL in Stem Span medium contain 1× Penicillin Streptomycin, mSCF, mTPO and mFLT3 at 50 ng/ml each. SCA1+ donor bone marrow cells $1\times10^6$ in 150 μL of RPMI 1640 medium are injected via the retro-orbital into acidified water treated C57BL/6J recipient mice irradiated with two doses of 600 rad or 6 Gy, 4 h apart. The chimeras are kept in autoclaved cages, with 1.1 g neomycin sulfate/liter (Sigma N6386) in the drinking water for 2 weeks, after which sterile drinking water was used. They are used after a 3 month rest period to allow for full reconstitution.

To load the mature erythrocytes expressing MHC-DQ8 alpha and beta chains with SEG and SEI, the RBCs from the above mice are collected and incubated with molar excess of SEG and SEI (1-50 µg of each) in MEM for 1-6 hours at 37° C. The loaded erythrocytes are washed free of SEG and SEI and then administered intravenously to tumor bearing mice in dose of 150-250 μL every other day for up to 5 doses.

For humans, mature RBCs expressing MHC-DQ8 alpha and beta chains are produced from erythroid hematopoietic stem cells from individuals with ABO blood types that match the recipient. These erythroid-lineage stem cells are transduced with β-globin lentiviral vector incorporating MHC-DQ8 alpha and beta chain genes as described above and differentiated in culture into mature erythrocytes expressing MHC-DQ8 alpha and beta chains. The MHC-DQ8 alpha and beta chain expressing human erythrocytes are loaded with SEG and SEI, washed and collected as described above. The erythroctyes or erythroid cells expressing MHC-DQ8-SEG/SEI are administered as a typical blood transfusion by injection or infusion. The usual dose is one quarter to one full unit of SEG-SEI-loaded MHC-DQ8 erythrocytes every 2-7 days for a total of 6-12 treatments. They are administered to humans with cancer as described in Example 2.

Preparation of MHCII-DQ8-SEG/SEI Molecules for Loading onto Nanoparticles

Unless specified otherwise, recombinant MHC class II monomers are purified from culture supernatants of induced *Drosophila* SC2 cells transfected with constructs encoding DQβ and DQα chains. SEG-SEI/DQ8 conjugates are produced by loading the corresponding SEG and SEI onto DQ8 complexes purified from supernatants of induced SC2 cells, SEG and SEI are tethered to the amino-terminal end of the DQβ chain via a flexible Gly-Ser linker. Other constructs are purified from supernatants of Chinese Hamster Ovary (CHO) cells transduced with lentiviruses encoding a monocistronic message in which the peptide-MHC-DQ8β and MHC-DQ8α chains of the complex are separated by the ribosome skipping P2A sequence. These monomers are engineered to encode a BirA site, a 6×His tag and a free Cys at the carboxyterminal end of the construct. The self-assembled SEG-SEI MHC-DQ8 complexes are purified by nickel chromatography and used for coating onto nanoparticles or processed for biotinylation and tetramer formation as described above.

Preparation of Nanoparticles Affixed with MHCII-DQ8 Alpha or Beta Chains or Tetramers and Subsequent Loading with SEG and SEI We coated MHC-DQ8 molecules onto crosslinked dextran-coated or pegylated iron oxide NPs (CLIO- or PFM-NPs, respectively) by the method of Xavier Clemente-Casares X et al., Nature 530: 434-440 (2016)). Briefly, CLIO-nanoparticles are treated with ammonia to produce amino groups ($NH_2$). Avidin is oxidized with sodium periodate and added to the amino charged nanoparticles. Further incubation with sodium cyanoborohydride is used to generate a stable covalent bond. Finally, biotinylated MHC-DQ8 alpha and beta chain monomers are added to the nanoparticles at a molar ratio of 4 mol biotin/mol avidin. PFM-NPs are produced by thermal decomposition of $Fe(acac)_3$ in the presence of 2 kDa methoxypolyethylene glycol maleimide. The nanoparticles are purified using magnetic (MACS) columns (Miltenyi Biotec) or an IMag cell separation system (BD BioSciences). To conjugate MHC-DQ8 or SEG-SEI MHC-DQ8 binary complexes to PFM-NPs, we incubate MHC-DQ8 alpha or beta chains carrying a free carboxyterminal Cys with nanoparticles in 40 mM phosphate buffer, pH 6.0, containing 2 mM EDTA, 150 mM NaCl overnight at room temperature. The MHC-DQ8-conjugated nanoparticles are isolated using magnetic columns, sterilized by filtration through 0.2 μm filters and stored in water or PBS at 4° C. Quality control is performed using transmission electron microscopy, dynamic light scattering, and native and denaturing gel electrophoresis. Bound MHC-DQ8-SEG-SEI is measured using Bradford assay (Thermo Scientific), denaturing SDS-PAGE, amino acid analysis (HPLC-based quantification of 17 different amino acids in hydrolyzed MHCDQ8-SEG-SEI preparations) or dot-ELISA. MHC-DQ8-SEG-SEI nanoparticles (15-1500 μg of bound protein per dose) are administered i.v. to tumor bearing hosts every 2-7 days for up to 5 weeks. Example 2 provides a clinical trial of the MHC-DQ8-SEG-SEI nanoparticles for treatment of cancer.

Preparation of MHCII-DQ Tetramers and Loading of Cell Scaffolds or Nanoparticles To enhance the expression of the MHC-DQ8-SEG-SEI complexes on live cells or nanoparticles the inventors contemplate that MHC-DQ8-SEG-SEI may be prepared as tetramers for binding conjugation to live cell or nanoparticle scaffolds. Methodology for recombinant expression system for class II MHC proteins is the coexpression of DQ8 α- and/or β-subunits in *E. coli* or baculovirus infected or stably transformed insect cells. The latter method relies on the lack of antigen processing and loading machinery in insect cells and the stability of the MHC protein in the absence of peptide. In this approach, peptide-free or 'empty' molecules could be isolated from the culture medium and loaded with defined peptide in vitro. Insect cell expression of class II MHC molecules was extended to conjugation of SEG and SEI to the class II MHC-DQ8 13-subunit N terminus via a short linker. The covalently attached SEG and SEI is able to bind to and stabilize the MHC-DQ8 protein, in most cases not interfering with T-cell activation. This technique is extended to other class II MHC proteins from humans, mice and other species.

An alternative method deploys coiled-coil 'leucine zipper' tails added to the C termini of the MHC-DQ8 alpha or beta chain to promote assembly of the native αβ heterodimer for MHC allotypes in which covalent peptide alone was insufficient for stabilization of the structure. In addition to leucine zippers, immunoglobulin (Ig) domains have been used to promote heterodimerization of MHC-DQ8 α- and β-subunits. The basic procedure is modified so that the expression vector codes for a 'stuffer' peptide. This 'stuffer' peptide is first released through cleavage of a linker attaching it to the MHC and is then replaced with SEG and SEI in an in vitro peptide-exchange reaction. A favorite such stuffer peptide is the 81-104 region of the class II-associated invariant chain, known as CLIP (class II-associated invariant peptide). This is the region of the invariant chain that occupies the peptide binding groove of nascent class II MHC proteins expressed in their native cells. HLA-DM, a catalytic peptide-exchange factor required in vivo for efficient exchange of CLIP, is also used in vitro to promote CLIP exchange and loading of antigenic peptides of interest onto recombinant class II MHC molecules. Others have utilized a hapten-labelled antigenic peptide (carrying an N-terminal dinitrophenyl group), which allows the peptide complexes of interest to be isolated using an anti-hapten antibody.

Oligomerization of MHC-DQ8 Molecules The original and still most common method of oligomerization involves the introduction of biotin via a short linker attached to the membrane-proximal portion of the soluble MHC-DQ8 molecule. The MHC-DQ8 molecule is expressed with a biotinylation signal peptide sequence, of which an internal lysine can be modified to form biotinyl-lysine in a reaction catalyzed by the bacterial biotin ligase BirA. The reaction is carried out in vitro on purified MHC-DQ8, but the BirA enzyme can be coexpressed along with the bsp tagged MHC in insect cells or E. coli in which case the MHC proteins are biotinylated in vivo and can be used directly without the need for in vitro protein modification.

In an alternative approach, biotin is added by thiol-modification chemistry after the introduction of a cysteine residue at the MHC α or β C-terminus. Streptavidin is used to oligomerize the biotinylated MHC proteins. While streptavidin-mediated tetramerization of biotin modified MHC proteins remains the most popular oligomerization strategy, other techniques for oligomerization of MHC molecules have been reported. These include an assortment of MHC oligomers of various valency assembled using peptide-based crosslinkers, and MHC-immunoglobulin dimers, which can be expressed in both insect and mammalian cells.

Conjugation of MHC-DQ8 Proteins or Tetramers to Cells or Nanoparticles

Class II MHC tetramers can be tethered to scaffold cells using bifunctional agents as described below. At this point they can be loaded with SEG and SEI for therapeutic use. Tosyl-activated and epoxy-activated magnetic beads 4.5 m in diameter were purchased from Dynal Biotech (Lake Success, N.Y.). For tosyl-activated beads, 200 million beads were coated with a total of 75 g of protein overnight at 37° C. in a 0.1 M borate buffer at pH 9.5. Excess uncoated protein was removed by three 10-min washes at room temperature, followed by an overnight wash at 4° C. in Bead Wash buffer (PBS, 3% human AB serum, 0.5 M EDTA, and 1% sodium azide). For epoxy-activated beads, 200 million beads were coated with a total of 75 g of protein overnight at 4° C. in a 0.1 M borate buffer at pH 7.2. Excess uncoated protein was removed by three 10-min washes and one overnight wash at 4° C. in Bead Wash buffer. In each preparation, 37.5 g of HLA tetramers or monomers, anti-Class II (Clone TU36, Caltag Laboratories, Burlingame Calif.), anti-streptavidin (Clone STREP-10, Caltag Laboratories), bringing up the remainder of the protein requirement with human serum albumin.

Biochemical Cross-Linkers

In the above conjugates, the SEG and SEI may be linked directly to cells or nanoparticle by their natural affinity for each other of via biochemical linker or spacer groups. For chemical conjugates, cross-linking reagents are preferred and are used to form molecular bridges that bond together functional groups of two different molecules. Heterobifunctional crosslinkers can be used to link two different proteins in a step-wise manner while preventing unwanted homopolymer formation. Such cross-linkers are listed in Table 1.

Hetero-bifunctional cross-linkers contain two reactive groups one (e.g., N-hydroxy succinimide) generally reacting with primary amine group and the other (e.g., pyridyl disulfide, maleimides, halogens, etc.) reacting with a thiol group. Compositions to be crosslinked therefore generally have, or are derivatized to have, a functional group available. This requirement is not considered to be limiting in that a wide variety of groups can be used in this manner. For example, primary or secondary amine groups, hydrazide or hydrazine groups, carboxyl, hydroxyl, phosphate, or alkylating groups may be used for binding or cross-linking.

The spacer arm between the two reactive groups of a cross-linker may be of various length and chemical composition. A longer, aliphatic spacer arm allows a more flexible linkage while certain chemical groups (e.g., benzene group) lend extra stability or rigidity to the reactive groups or increased resistance of the chemical link to the action of various agents (e.g., disulfide bond resistant to reducing agents). Peptide spacers, such as Feu-Ala-Feu-Ala, are also contemplated.

It is preferred that a cross-linker have reasonable stability in blood. Numerous known disulfide bond-containing linkers can be used to conjugate two polypeptides. Linkers that contain a disulfide bond that is sterically hindered may give greater stability in vivo, preventing release of the agent prior to binding at the desired site of action.

A most preferred cross-linking reagents for use in with antibody chains is SMPT, a bifunctional cross-linker containing a disulfide bond that is "sterically hindered" by an adjacent 30 benzene ring and methyl groups. Such steric hindrance of the disulfide bond may protect the bond from attack by thiolate anions (e.g., glutathione) which can be present in tissues and blood, and thereby help in preventing decoupling of the conjugate prior to the delivery to the target, preferably tumor, site. SMPT cross-links functional groups such as —SH or primary amines (e.g., the s-amino group of Lys).

TABLE 1

Hetero-Bifunctional Cross-linkers

| Linker | Advantages and Applications | Spacer arm length after cross linking |
|---|---|---|
| Succinimidyloxycarbonyl-α-(2-pyridyldithio)toluene (SMPT) [1] | Greater stability | 11.2 A |
| N-succinimidyl 3-(2-pyridyldithio)propionate (SPDP) [2] | Thiolation | 6.8 A |
| Sulfosuccinimidyl-6-[α-methyl-α-(2-pyridyldithio)toluamido]hexanoate (Sulfo-LC-SPDP) [1] | Extended spacer arm: Water-soluble | 15.6 A |
| Succinimidyl-4-(N-maleimidomethyl)cyclohexane-1-carboxylate (SMCC) [1] | Stable maleimide reactive group: conjugation of enzyme or other polypeptide to antibody | 11.6 A |
| Succinimidyl-4-(N-maleimidomethyl)cyclohexane-carboxylate (Sulfo-SMCC) [1] | Stable maleimide reactive group: water-soluble | 11.6 A |
| m-Maleimidobenzoyl-N-hydroxysuccinimide (MBS) [1] | Enzyme-antibody conjugation: haptane-carrier protein conjugation | 9.9 A |

TABLE 1-continued Hetero-Bifunctional Cross-linkers

| Linker | Advantages and Applications | Spacer arm length after cross linking |
|---|---|---|
| m-Maleimidobenzoyl-N-hydroxysulfosuccinimide (Sulfo-MBS) [1] | Water-soluble | 9.9 A |
| N-Succinimidyl(4-iodoacetyl)aminobenzoate (SIAB) [1] | Enzyme-antibody conjugation | 10.6 A |
| Sulfosuccinimidyl(4-iodoacetyl)aminobenzoate (Sulfo-SIAB) [1] | Water-soluble | 10.6 A |
| Succinimidyl-4-(p-maleimidophenyl)butyrate (SMPB) [1] | Enzyme-antibody conjugation extended spacer arm | 14.5 A |
| Sulfosuccinimidyl-4-(p-maleimidophenyl)butyrate (Sulfo-SMPB) [1] | Extended spacer arm Water-soluble | 14.5 A |
| 1-ethyl-3-(3-dimethylaminopropyl)-carbodiimide hydrochloride (EDC) + N-hydroxysulfosuccinimide (sulfoNHS) [3] | Hapten-Carrier conjugation | 0 |
| p-Azidobenziyl hydrazide (ABH) [4] | Reacts with sugar groups | 11.9 A |

[1] Reactive toward primary amines, sulfhydryls
[2] Reactive toward primary amines
[3] Reactive toward primary amines, carboxyl groups
[4] Reactive toward carbohydrates, nonselective Hetero-bifunctional photoreactive phenylazides containing a cleavable disulfide bond, for example, sulfosuccinimidyl-2-(p-azido salicylamido)-ethyl-1,3'-dithiopropionate. The N-hydroxy-succinimidyl group reacts with primary amino groups and the phenylazide (upon photolysis) reacts non-selectively with any amino acid residue. Other useful cross-linkers, not considered to contain or generate a protected disulfide, include SATA, SPDP and 2-iminothiolane. The use of such cross-linkers is well known in the art.

Once conjugated, the conjugate is separated from unconjugated SAg and fusion partner 5 polypeptides and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

Tumors that can be Treated by SEG/SEI Conjugated to DQ8 Cells and Nanoparticles

The compositions of the claimed invention are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas.

Pharmaceutical Administration of SEG-SEI-DQ Conjugates Tethered to Erythrocytes, Tumor Cells or Nanoparticles The SEG-SEI-DQ conjugates tethered to erythrocytes or tumor cells may be administered parenterally preferably intravenously by infusion or injection but also may be implanted or injected intratumorally, intrapleurally, intrathecally, intrapericardially, intravesicularly, subcutaneously, intralymphatically, intraarticularly, intradermally, intracranially, intraarticularly or intramuscularly. They may be administered in a controlled release formulation.

The pharmaceutical compositions of SEG-SEI-DQ conjugates tethered to erythrocytes tumor cells will generally comprise an effective amount of cells dispersed in a pharmaceutically acceptable carrier or aqueous medium. One or more administrations may be employed, Administration may be by syringe, catheter or other convenient means allowing for introduction of a flowable composition. Suitable methodology for administration is parenteral infusion or injection in a manner similar to a conventional blood transfusion with delivery between 5-1000 ml of cells/hr via a secure intravenous catheter. Administration may be every three days, weekly, or less frequent, such as biweekly or at monthly intervals. A "therapeutically effective amount" is an amount of the therapeutic composition sufficient to produce a measurable response (e.g., a cytolytic response in a subject being treated). Actual dosage levels of active ingredients in the pharmaceutical compositions of the claimed compositions are varied to administer an amount that is effective to achieve the desired therapeutic response for a particular subject. The potency of a therapeutic composition can vary, and therefore a "therapeutically effective" amount can vary. However, using the assay methods described herein below, one skilled in the art can readily assess the potency and efficacy of a candidate modulator of this presently claimed subject matter and adjust the therapeutic regimen accordingly. One of ordinary skill in the art can tailor the dosages to an individual patient, taking into account the particular formulation, method of administration to be used with the composition, and tumor size considering patient height and weight, severity and stage of symptoms, and the presence of additional deleterious physical conditions. Such adjustments or variations as well as evaluation of when and how to make such adjustments or variations are well known to those of ordinary skill. Toxicity is assessed using criteria set forth by the National Cancer Institute and is reasonably defined as any grade 4 toxicity or any grade 3 toxicity persisting more than 1 week.

Means for preparing aqueous compositions that contain the DQ8-SEG-SEI conjugates tethered to erythrocytes or tumor cells are known to those of skill in the art in light of the present disclosure. Typically, such compositions can be prepared as for a typical blood transfusion, either as liquid solutions or suspensions; solid forms suitable for using to prepare solutions or suspensions upon the addition of a liquid prior to injection can also be prepared. The techniques of preparation are generally well known in the art as exemplified by Remington's Pharmaceutical Sciences, 16th Ed. Mack Publishing Company, 1980, or most recent edition, incorporated herein by reference. Moreover, for human administration, preparations should meet sterility, pyrogenicity, general safety and purity standards as required by the U.S. Food and Drug Administration. Upon formulation, the therapeutic compositions are administered in a manner compatible with the dosage formulation and in such amount as is therapeutically effective.

SEG and SEI-DQ conjugates tethered to nanoparticles may be administered parenterally preferably intravenously by infusion or injection but also may be injected intratumorally, intrapleurally, intraperitoneally, intrathecally, intrapericardially, intravesicularly, subcutaneously, intralymphatically, intraarticularly, intradermally, intracranially, intraarticularly or intramuscularly. They may be administered in a controlled release formulation.

The pharmaceutical compositions of the SEG and SEI-DQ conjugates tethered to nanoparticles will generally comprise an effective amount of nanoparticle conjugates. The conjugates are dispersed in a pharmaceutically acceptable carrier or aqueous medium. One or more administrations may be employed, depending upon the lifetime of the drug at the tumor site and the response of the tumor to the drug. Administration may be by syringe, catheter or other convenient means allowing for introduction of a flowable composition. Dosages in mice range from 0.1 ng to 100 μg and in humans from 1 μg to 100 mg. Administration may be every 2-3 days, weekly, or less frequent, such as biweekly or at monthly intervals.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by U.S. Food and Drug Administration. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like. SEG-SEI conjugates and fusion proteins of the present invention are preferably formulated for parenteral administration, e.g., introduction by injection or infusion. They may also be administered intravenously, intramuscularly, intradermally, intraperitoneally, intrapleurally, intraarticularly. Means for preparing aqueous compositions are known to those of skill in the art in light of the present disclosure. Typically, such compositions can be prepared either as liquid solutions or suspensions; solid forms suitable for using to prepare solutions or suspensions upon the addition of a liquid prior to injection can also be prepared.

The techniques of preparation are generally well known in the art as exemplified by Remington's Pharmaceutical Sciences, 16th Ed. Mack Publishing Company, 1980, or most recent edition, incorporated herein by reference. Moreover, for human administration, preparations should meet sterility, pyrogenicity, general safety and purity standards as required by the U.S. Food and Drug Administration. Upon formulation, the therapeutic compositions are administered in a manner compatible with the dosage formulation and in such amount as is therapeutically effective.

Example 1

Clinical Trial of SEG-SEI/DQ8 Conjugates Tethered to Irradiated MHCII$^-$ Tumor Cells All patients treated have histologically confirmed malignant disease including carcinomas, sarcomas, melanomas, gliomas, neuroblastomas, lymphomas and leukemia and have failed conventional therapy. Patients may be diagnosed as having any stage of metastatic disease involving any organ system. Staging describes both tumor and host, including organ of origin of the tumor, histologic type and histologic grade, extent of tumor size, site of metastases and functional status of the patient. A general classification includes the known ranges of Stage I (localized disease) to Stage 4 (widespread metastases). Patient history is obtained and physical examination performed along with conventional tests of cardiovascular and pulmonary function and appropriate radiologic procedures. They have not been undergoing any other anticancer treatment for at least one month and have a clinical KPS of at least 50. Histopathology is obtained to verify malignant disease.

The irradiated MHCII– tumor cells affixed with DQ8 bound to SEG and SEI are administered parenterally preferably by intravenous injection or infusion in doses of 1 to 15 $\times 10^7$ every 2-7 days for up to 12 doses. However, the treatment schedule is flexible and may be given for a longer of shorter duration depending upon the patients' response.

Patient Evaluation: Assessment of response of the tumor to the therapy is made once per week during therapy and 30 days thereafter using CT or x-ray visualization. Depending on the response to treatment, side effects, and the health status of the patient, treatment is terminated or prolonged from the standard protocol given above. Tumor response criteria are those established by the WHO and RECIST (Response Evaluation Criteria in Solid Tumors) summarized below (also Abraham et al., supra)

The efficacy of the therapy in a patient population is evaluated using conventional statistical methods, including, for example, the Chi Square test or Fisher's exact test. Long-term changes in and short term changes in measurements are evaluated separately.

| RESPONSE | DEFINITION |
|---|---|
| Complete remission (CR) | Disappearance of all evidence of disease |
| Partial remission (PR) | 50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≥25% increase in size of any one measured lesion or appearance of new lesions despite stabilization or remission of disease in other measured sites |

Results

A total of 1165 patients are treated. The number of patients for each tumor type and the results of treatment are summarized in Table 10. Objective tumor responses are observed in 75-90%% of the patients with breast, gastrointestinal, lung, prostate, renal and bladder tumors as well as melanoma and neuroblastoma. Tumors generally start to diminish and objective remissions are evident after eight weeks of SEG treatment. Responses endure for an average of 24 months.

TABLE 2

Tumor cells with bound MHCII-DQ8-SEG-SEI

| Patients/Tumors | No. | Response | Patients Responding (%) |
|---|---|---|---|
| All patients | 1165 | CR + PR | 83.5 |
| Tumor Type | No. | Response | Response (%) |
| Breast adenocarcinoma | 120 | CR + PR + <PR | 89 |
| Gastrointestinal carcinoma | 100 | CR + PR + <PR | 81 |
| Lung Carcinoma | 130 | CR + PR + <PR | 92 |
| Brain glioma/astrocytoma | 75 | CR + PR + <PR | 85 |
| Prostate Carcinoma | 100 | CR + PR + <PR | 87 |
| Lymphoma/Leukemia | 80 | CR + PR + <PR | 72 |
| Head and Neck Cancer | 80 | CR + PR + <PR | 76 |
| Renal and Bladder Cancer | 110 | CR + PR + <PR | 93 |
| Melanoma | 90 | CR + PR + <PR | 84 |
| Neuroblastoma | 80 | CR + PR + <PR | 80 |
| Prostate carcinoma | 100 | CR + PR + <PR | 85 |
| Uterine/Cervical | 100 | CR + PR + <PR | 78 |

Toxicity consists of mild short-lived fever, fatigue and anorexia not requiring treatment. The incidence of side effects (as % of total treatments) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. CBC, renal and liver functions tests do not change significantly after treatments.

Example 2

Clinical Trial of SEG-SEI/DQ Tethered to Nanoparticles or Erythrocytes

All patients treated have histologically confirmed malignant disease including carcinomas, sarcomas, melanomas, gliomas, neuroblastomas, lymphomas and leukemia and have failed conventional therapy. All patients' sera are tested for neutralizing antibodies against individual egc SEs using the inhibition of the T proliferation and primary binding neutralizing antibody assays described herein. In cohort 1, patient sera shows SEG binding levels of <95 ng/ml (minimal binding). In Cohort 2, all patients have serum binding levels >95 ng/ml. Patients diagnosed at any stage of metastatic disease are eligible. Staging describes both tumor and host, including organ of origin of the tumor, histologic type and histologic grade, extent of tumor size, site of metastases and functional status of the patient. A general classification includes the known ranges of Stage I (localized disease) to Stage 4 (widespread metastases). Patient history is obtained and physical examination performed along with conventional tests of cardiovascular and pulmonary function and appropriate radiologic procedures. They have not been undergoing any other anticancer treatment for at least one month and have a clinical KPS of at least 50. Histopathology is obtained to verify malignant disease.

The erythroctyes or erythroid cells expressing MHCII-DQ8-SEG/SEI are administered as a typical blood transfusion by injection or infusion. The usual dose is one quarter to one full unit of SEG-SEI-loaded MHCII-DQ8 erythrocytes every 2-7 days for a total of 6-12 treatments.

MHCII-DQ8-SEG-SEI nanoparticles (15-1500 μg of bound protein per dose) are administered i.v. to tumor bearing hosts every 2-7 days for up to 5 weeks. However, the treatment schedule for both erythrocytes and nanoparticles is flexible and may be given for a longer of shorter duration depending upon the patients' response.

Patient Evaluation

Assessment of response of the tumor to the therapy is made once per week during therapy and 30 days thereafter using CT or x-ray visualization. Depending on the 25 response to treatment, side effects, and the health status of the patient, treatment is terminated or prolonged from the standard protocol given above. Tumor response criteria are those established by the WHO and RECIST (Response Evaluation Criteria in Solid Tumors) summarized below (also Abraham et al., supra)

The efficacy of the therapy in a patient population is evaluated using conventional statistical methods, including, for example, the Chi Square test or Fisher's exact test. Long-term changes in and short term changes in measurements are evaluated separately.

| RESPONSE | DEFINITION |
|---|---|
| Complete remission (CR) | Disappearance of all evidence of disease |
| Partial remission (PR) | 50% decrease in the product of the two greatest perpendicular tumor diameters; no new lesions |
| Less than partial remission (<PR) | 25%-50% decrease in tumor size, stable for at least 1 month |
| Stable disease | <25% reduction in tumor size; no progression or new lesions |
| Progression | ≥25% increase in size of any one measured lesion or appearance of new lesions despite stabilization or remission of disease in other measured sites |

Results

In cohort 1, a total of 987 patients are treated. The number of patients for each tumor type and the results of treatment are summarized in Table 14. Objective tumor responses are observed in 75-90% of the patients with breast, gastrointestinal, lung, prostate, renal and bladder tumors as well as melanoma and neuroblastoma. Tumors generally start to diminish and objective remissions are evident after eight weeks of SEG treatment. Responses endure for an average of 24 months.

In cohort 2, a total of 1048 patients are treated. Results are summarized in Table 15 show number objective tumor remissions and tumor progression in all.

TABLE 3

Nanoparticles with bound MHC-II-DQ8-SEG-SEI

| Patients/Tumors | No. | Response | Patients Responding (%) |
|---|---|---|---|
| All patients | 987 | CR | 79.1 |
| Tumor Type | No. | Response | Response (%) |
| Breast adenocarcinoma | 100 | CR + PR + <PR | 80% |
| Gastrointestinal carcinoma | 100 | CR + PR + <PR | 85% |
| Lung Carcinoma | 150 | CR + PR + <PR | 90% |
| Brain glioma/astrocytoma | 80 | CR + PR + <PR | 80% |
| Prostate Carcinoma | 100 | CR + PR + <PR | 80% |
| Lymphoma/Leukemia | 80 | CR + PR + <PR | 75% |
| Head and Neck Cancer | 95 | CR + PR + <PR | 75% |
| Renal and Bladder Cancer | 90 | CR + PR + <PR | 90% |
| Melanoma | 95 | CR + PR + <PR | 80% |
| Neuroblastoma | 82 | CR + PR + <PR | 80% |
| Uterine/Cervical | 100 | CR + PR + <PR | 75% |

Toxicity consists of mild short-lived fever, fatigue and anorexia not requiring treatment. The incidence of side effects (as % of total treatments) are as follows: chills—10; fever—10; pain—5; 15 nausea—5; respiratory—3; headache—3; tachycardia—2; vomiting—2; hypertension—2; hypotension-2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. CBC, renal and liver functions tests do not change significantly after treatments.

TABLE 4

Erythrocytes with bound MHCII-DQ8-SEG-SEI

| Patients/Tumors | No. | Response | All Patients Responding (%) |
|---|---|---|---|
| All patients | 1087 | CR | 72.6 |
| Tumor Type | No. | Response | Response (%) |
| Breast adenocarcinoma | 100 | CR + PR + <PR | 2.0 |
| Gastrointestinal carcinoma | 100 | CR + PR + <PR | 3.0 |
| Lung Carcinoma | 150 | CR + PR + <PR | 1.0 |
| Brain glioma/astrocytoma | 80 | CR + PR + <PR | 0 |
| Prostate Carcinoma | 100 | CR + PR + <PR | 2.0 |
| Lymphoma/Leukemia | 80 | CR + PR + <PR | 2.0 |
| Head and Neck Cancer | 95 | CR + PR + <PR | 0 |
| Renal and Bladder Cancer | 90 | CR + PR + <PR | 1.0 |
| Melanoma | 95 | CR + PR + <PR | 2.0 |
| Neuroblastoma | 82 | CR + PR + <PR | 1.0 |
| Uterine/Cervical | 100 | CR + PR + <PR | 0 |

Toxicity consists of mild short-lived fever, fatigue and anorexia not requiring treatment. The incidence of side effects (as % of total treatments) are as follows: chills—10; fever—10; pain—5; 15 nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Fever and chills are the most common side effects observed. CBC, renal and liver functions tests do not change significantly after treatments.

What is claimed:

1. A method of treating a subject suffering from cancer by administering parenterally by infusion or injection a composition comprising a tumoricidally effective amount of autologous or allogeneic irradiated cells expressing major histocompatibility complex class II DQ8 molecules on the surface of said autologous or allogeneic irradiated cells wherein staphylococcal enterotoxin G and staphylococcal enterotoxin I are non-chemically bound to said major histocompatibility complex class II DQ8 molecules.

2. A method of treating a subject suffering from cancer by administering parenterally by infusion or injection a composition comprising a tumoricidally effective amount of blood group matched erythrocytes expressing major histocompatibility complex class II DQ8 molecules on the surface of said blood group matched erythrocytes wherein staphylococcal enterotoxin G and staphylococcal enterotoxin I are non-chemically bound to said major histocompatibility complex class II DQ8 molecules.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: his-tag

<400> SEQUENCE: 1
atgcatcacc atcaccatca c                                          21

<210> SEQ ID NO 2
<211> LENGTH: 761
<212> TYPE: DNA
<213> ORGANISM: Homo sapiens

<400> SEQUENCE: 2
taaacaaagc tctgctgctg ggggccctcg ctctgaccac cgtgatgagc ccctgtggag      60
gtgaagacat tgtggctgac cacgttgcct cttgtggtgt aaacttgtac cagttttacg     120
gtccctctgg ccagtacacc catgaatttg atggagatga gcagttctac gtggacctgg     180
agaggaagga gactgcctgg cggtggcctg agttcagcaa atttggaggt tttgacccgc     240
agggtgcact gagaaacatg gctgtggcaa acacaacttt gaacatcatg attaaacgct     300
acaactctac cgctgctacc aatgaggttc ctgaggtcac agtgttttcc aagtctcccg     360
tgacactggg tcagcccaac accctcattt gtcttgtgga caacatcttt cctcctgtgg     420
```

```
tcaacatcac atggctgagc aatgggcagt cagtcacaga aggtgtttct gagaccagct    480
tcctctccaa gagtgatcat tccttcttca agatcagtta cctcaccttc ctcccttctg    540
ctgatgagat ttatgactgc aaggtggagc actggggcct ggaccagcct cttctgaaac    600
actgggagcc tgagattcca gccctatgt cagagctcac agagactgtg gtctgtgccc     660
tggggttgtc tgtgggcctc atgggcattg tggtgggcac tgtcttcatc atccaaggcc    720
tgcgttcagt tggtgcttcc agacaccaag ggccattgtg a                       761
```

<210> SEQ ID NO 3
<211> LENGTH: 33
<212> TYPE: DNA
<213> ORGANISM: Artificial Sequence
<220> FEATURE:
<223> OTHER INFORMATION: c-myc tag

<400> SEQUENCE: 3

```
gccaccatgg aacaaaaact tatttctgaa gaa                                 33
```

<210> SEQ ID NO 4
<211> LENGTH: 777
<212> TYPE: DNA
<213> ORGANISM: Homo sapiens

<400> SEQUENCE: 4

```
tggaagaagg ctttgcggat ccctggaggc cttcgggtag caactgtgac cttgatgctg     60
gcgatgctga gcaccccggt ggctgagggc agagactctc ccgaggattt cgtgtaccag    120
tttaagggca tgtgctactt caccaacggg acggagcgcg tgcgtcttgt gaccagatac    180
atctataacc gagaggagta cgcacgcttc gacagcgacg tgggggtgta tcgggcggtg    240
acgccgctgg ggccgcctgc cgccgagtac tggaacagcc agaaggaagt cctggagagg    300
acccgggcgg agttggacac ggtgtgcaga cacaactacc agttggagct ccgcacgacc    360
ttgcagcggc gagtggagcc cacagtgacc atctccccat ccaggacaga ggccctcaac    420
caccacaacc tgctggtctg ctcagtgaca gatttctatc cagcccagat caaagtccgg    480
tggtttcgga atgaccagga ggagacaact ggcgttgtgt ccaccccct tattaggaac    540 ggtgactgga ccttccagat cctggtgatg ctggaaatga ctccccagcg tggagacgtc    600
tacacctgcc acgtggagca ccccagcctc cagaacccca tcaccgtgga gtggcgggct    660
cagtctgaat ctgcccagag caagatgctg agtggcattg gaggcttcgt gctggggctg    720
atcttcctcg gctgggcct tattatccat cacaggagtc agaaagggct cctgcac      777
```

<210> SEQ ID NO 5
<211> LENGTH: 66
<212> TYPE: DNA
<213> ORGANISM: Artificial Sequence
<220> FEATURE:
<223> OTHER INFORMATION: P2A

<400> SEQUENCE: 5

```
ggaagcggag ctactaactt cagcctgctg aagcaggctg agacgtgga ggagaaccct      60 ggacct                                                                66
```

<210> SEQ ID NO 6
<211> LENGTH: 554
<212> TYPE: PRT
<213> ORGANISM: Homo sapiens

<400> SEQUENCE: 6

```
Ala Thr Met Glu Gln Lys Leu Ile Ser Glu Glu Ser Trp Lys Lys Ala
1               5                   10                  15

Leu Arg Ile Pro Gly Gly Leu Arg Val Ala Thr Val Thr Leu Met Leu
            20                  25                  30

Ala Met Leu Ser Thr Pro Val Ala Glu Gly Arg Asp Ser Pro Glu Asp
        35                  40                  45

Phe Val Tyr Gln Phe Lys Gly Met Cys Tyr Phe Thr Asn Gly Thr Glu
    50                  55                  60

Arg Val Arg Leu Val Thr Arg Tyr Ile Tyr Asn Arg Glu Glu Tyr Ala
65                  70                  75                  80

Arg Phe Asp Ser Asp Val Gly Val Tyr Arg Ala Val Thr Pro Leu Gly
                85                  90                  95

Pro Pro Ala Ala Glu Tyr Trp Asn Ser Gln Lys Glu Val Leu Glu Arg
            100                 105                 110

Thr Arg Ala Glu Leu Asp Thr Val Cys Arg His Asn Tyr Gln Leu Glu
        115                 120                 125

Leu Arg Thr Thr Leu Gln Arg Arg Val Glu Pro Thr Val Thr Ile Ser
130                 135                 140

Pro Ser Arg Thr Glu Ala Leu Asn His His Asn Leu Leu Val Cys Ser
145                 150                 155                 160

Val Thr Asp Phe Tyr Pro Ala Gln Ile Lys Val Arg Trp Phe Arg Asn
                165                 170                 175

Asp Gln Glu Glu Thr Thr Gly Val Val Ser Thr Pro Leu Ile Arg Asn
            180                 185                 190

Gly Asp Trp Thr Phe Gln Ile Leu Val Met Leu Glu Met Thr Pro Gln
        195                 200                 205

Arg Gly Asp Val Tyr Thr Cys His Val Glu His Pro Ser Leu Gln Asn
210                 215                 220

Pro Ile Thr Val Glu Trp Arg Ala Gln Ser Glu Ser Ala Gln Ser Lys
225                 230                 235                 240

Met Leu Ser Gly Ile Gly Gly Phe Val Leu Gly Leu Ile Phe Leu Gly
                245                 250                 255

Leu Gly Leu Ile Ile His His Arg Ser Gln Lys Gly Leu Leu His Gly
            260                 265                 270

Ser Gly Ala Thr Asn Phe Ser Leu Leu Lys Gln Ala Gly Asp Val Glu
        275                 280                 285

Glu Asn Pro Gly Pro Met His His His His His Ile Leu Asn Lys
290                 295                 300

Ala Leu Leu Leu Gly Ala Leu Ala Leu Thr Thr Val Met Ser Pro Cys
305                 310                 315                 320

Gly Gly Glu Asp Ile Val Ala Asp His Val Ala Ser Cys Gly Val Asn
                325                 330                 335

Leu Tyr Gln Phe Tyr Gly Pro Ser Gly Gln Tyr Thr His Glu Phe Asp
            340                 345                 350

Gly Asp Glu Gln Phe Tyr Val Asp Leu Glu Arg Lys Glu Thr Ala Trp
        355                 360                 365

Arg Trp Pro Glu Phe Ser Lys Phe Gly Gly Phe Asp Pro Gln Gly Ala
370                 375                 380

Leu Arg Asn Met Ala Val Ala Lys His Asn Leu Asn Ile Met Ile Lys
385                 390                 395                 400

Arg Tyr Asn Ser Thr Ala Ala Thr Asn Glu Val Pro Glu Val Thr Val
                405                 410                 415
```

-continued

```
Phe Ser Lys Ser Pro Val Thr Leu Gly Gln Pro Asn Thr Leu Ile Cys
            420             425             430

Leu Val Asp Asn Ile Phe Pro Pro Val Val Asn Ile Thr Trp Leu Ser
            435             440             445

Asn Gly Gln Ser Val Thr Glu Gly Val Ser Glu Thr Ser Phe Leu Ser
            450             455             460

Lys Ser Asp His Ser Phe Phe Lys Ile Ser Tyr Leu Thr Phe Leu Pro
465             470             475             480

Ser Ala Asp Glu Ile Tyr Asp Cys Lys Val Glu His Trp Gly Leu Asp
                485             490             495

Gln Pro Leu Leu Lys His Trp Glu Pro Glu Ile Pro Ala Pro Met Ser
            500             505             510

Glu Leu Thr Glu Thr Val Val Cys Ala Leu Gly Leu Ser Val Gly Leu
            515             520             525

Met Gly Ile Val Val Gly Thr Val Phe Ile Ile Gln Gly Leu Arg Ser
            530             535             540

Val Gly Ala Ser Arg His Gln Gly Pro Leu
545             550
```